US011911128B2

(12) United States Patent
Blaauw et al.

(10) Patent No.: US 11,911,128 B2
(45) Date of Patent: Feb. 27, 2024

(54) WIRELESS NEURAL RECORDING DEVICES AND SYSTEM WITH TWO STAGE RF AND NIR POWER DELIVERY AND PROGRAMMING

(71) Applicant: THE REGENTS OF THE UNIVERSITY OF MICHIGAN, Ann Arbor, MI (US)

(72) Inventors: David T. Blaauw, Ann Arbor, MI (US); Jamie Phillips, Ann Arbor, MI (US); Cynthia Anne Chestek, Ann Arbor, MI (US); Taekwang Jang, Ann Arbor, MI (US); Hun-Seok Kim, Ann Arbor, MI (US); Dennis Sylvester, Ann Arbor, MI (US); Jongyup Lim, Ann Arbor, MI (US); Eunseong Moon, Ann Arbor, MI (US); Michael Barrow, Ann Arbor, MI (US); Samuel Nason, Ann Arbor, MI (US); Julianna Richie, Ann Arbor, MI (US); Paras Patel, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 479 days.

(21) Appl. No.: 17/173,976

(22) Filed: Feb. 11, 2021

(65) Prior Publication Data

US 2021/0244280 A1    Aug. 12, 2021

Related U.S. Application Data

(60) Provisional application No. 62/975,333, filed on Feb. 12, 2020.

(51) Int. Cl.
*A61B 5/00* (2006.01)
*H04B 10/80* (2013.01)
(Continued)

(52) U.S. Cl.
CPC .......... *A61B 5/0017* (2013.01); *A61B 5/0006* (2013.01); *A61B 5/0031* (2013.01);
(Continued)

(58) Field of Classification Search
CPC ... A61B 5/0017; A61B 5/0006; A61B 5/0031; A61B 5/37; A61B 5/384;
(Continued)

(56) References Cited

U.S. PATENT DOCUMENTS 6,647,296 B2   11/2003   Fischell et al.
8,849,369 B2    9/2014   Cogan et al.
(Continued)

FOREIGN PATENT DOCUMENTS

WO    2019157397 A1   8/2019

OTHER PUBLICATIONS

Cash, Sydney S, and Leigh R Hochberg. "The emergence of single neurons in clinical neurology." Neuron vol. 86,1 (2015): 79-91. doi: 10.1016/j.neuron.2015.03.058.
(Continued)

*Primary Examiner* — Tejal Gami
(74) *Attorney, Agent, or Firm* — Harness, Dickey & Pierce, P.L.C.

(57) ABSTRACT

A mote includes an optical receiver that wirelessly receives a power and data signal in form of NIR light energy within a patient and converts the NIR light energy to an electrical signal having a supply voltage. A control module supplies the supply voltage to power devices of the mote. A clock generation circuit locks onto a target clock frequency based on the power and data signal and generates clock signals. A data recovery circuit sets parameters of one of the devices based on the power and data signal and a first clock signal. An amplifier amplifies a neuron signal detected via an electrode inserted in tissue of the patient. A chip identifier (Continued)

module, based on a second clock signal, generates a recorded data signal based on a mote chip identifier and the neuron signal. A driver transmits the recorded data signal via a LED or a RF transmitter.

31 Claims, 27 Drawing Sheets

(51) Int. Cl.
 *H04B 10/114* (2013.01)
 *A61B 5/37* (2021.01)
 *A61B 5/384* (2021.01)

(52) U.S. Cl.
 CPC ............... *A61B 5/37* (2021.01); *A61B 5/384* (2021.01); *H04B 10/114* (2013.01); *H04B 10/80* (2013.01); *A61B 2560/0219* (2013.01)

(58) Field of Classification Search
 CPC .......... A61B 2560/0219; H04B 10/114; H04B 10/80; H04B 10/807
 See application file for complete search history.

(56) References Cited

U.S. PATENT DOCUMENTS 9,819,074 B2 11/2017 Muller et al.
10,219,697 B2 3/2019 Muller

OTHER PUBLICATIONS

Morshed and Khan (2014) A Brief Review of Brain Signal Monitoring Technologies for BCI Applications: Challenges and Prospects. J Bioeng Biomed Sci 4: 128. doi: 10.4172/2155-9538. 1000128.
Rotermund, David et al. "Implications for a Wireless, External Device System to Study Electrocorticography." Sensors (Basel, Switzerland) vol. 17,4 761. Apr. 4, 2017, doi:10.3390/s17040761.
J. Lee, et al., "An Implantable Wireless Network of Distributed Microscale Sensors for Neural Applications," Int. IEEE/EMBS NER, pp. 871-874, Mar. 20-23, 2019.
J. Lee, et al., "Wireless Power and Data Link for Ensembles of Sub-mm scale Implantable Sensors near 1GHz," IEEE BioCAS, pp. 1-4, 2018.
M.M. Ghanbari, et al., "A 0.8mm2 Ultrasonic Implantable Wireless Neural Recording System with Linear AM Backscattering," ISSCC Dig. Tech. Papers, pp. 284-285, Feb. 19, 2019.
S. Lee, et al., "A 330μm×90μm Opto-Electronically Integrated Wireless System-on-Chip for Recording of Neural Activities," ISSCC Dig. Tech. Papers, pp. 292-293, Feb. 13, 2018.
"Chronic in vivo stability assessment of carbon fiber microelectrode arrays," by Paras R Patel, Huanan Zhang, Matthew T Robbins, Justin B Nofar, Shaun P Marshall, Michael J Kobylarek, Takashi D Y Kozai, Nicholas A Kotov, and Cynthia A Chestek, Journal of Neural Engineering 13 (2016).
E. J. Welle, A. A. Jiman, P. R. Patel, J. Woods, J. M. Richie, E. C. Bottorff, J. P. Seymour, T. M. Bruns, C. A. Chestek, "Fabrication and characterization of a carbon fiber peripheral nerve electrode appropriate for chronic recording." Program No. 522.06. 2019 Neuroscience Meeting Planner. Chicago, IL: Society for Neuroscience, Oct. 22, 2019. Online.
K. Yang, Q. Dong, D. Blaauw and D. Sylvester, "8.3 A 553F22-transistor amplifier-based Physically Unclonable Function (PUF) with 1.67% native instability," 2017 IEEE International Solid-State Circuits Conference (ISSCC), San Francisco, CA, Feb. 7, 2017, pp. 146-147.

Measured AC gain and input referred noise of amplifier

_In vivo_ transient measurement results with rat motor cortex neural signal

|  | This work | NER 2019 [7] | ISSCC 2019 [9] | ISSCC 2018 [11] |
|---|---|---|---|---|
| Technology [nm] | 180 | 65 | 65 | 180 |
| Wireless power source | Optical | RF | Ultrasonic | Optical |
| Data transmission method | Optical | RF | Ultrasonic | Optical |
| Data transmission Up-link | SIM (Symbol Interval Modulation) | BPSK-modulated RF backscatter | AM backscatter | PPM |
| Data transmission Down-link | PWM | ASK-PWM | No | No |
| On-chip feature extraction | SBP | No | No | No |
| Chip ID | 16b | 24b | No | No |
| Clock recovery | Yes | No | No | No |
| Supply [V] | 1.5 | 0.6 | 1 | 0.9 |
| Power [µW] Total | 0.74 | 40 | 28.8 | < 1 |
| Power [µW] Amplifier | 0.51 | 3.2 | 4 | < 0.52 |
| Area [mm²] ( W [mm] x L [mm] ) | 0.0323 (0.19 x 0.17) | 0.25 (0.5 x 0.5) | PZT: 0.5625 (0.75 x 0.75) IC: 0.25 (0.5 x 0.5) | 0.0297 (0.330 x 0.090) |
| Target neural signal | AP | ECoG (epicortical) | LFP, AP | LFP, AP |
| Gain [dB] | 69 | N/A | 24 | 24 |
| Bandwidth [Hz] | 180 ~ 950* | 500 | 5000 | 10000 |
| Input referred noise [µVrms] | 4.8† | 2.2 | 5.3 | 42 |
| NEF | 3.76 | 8.7 | 5.87 | 12.3 |

* -10dB cutoff frequency
† Output noise divided by transfer function

FIG. 21

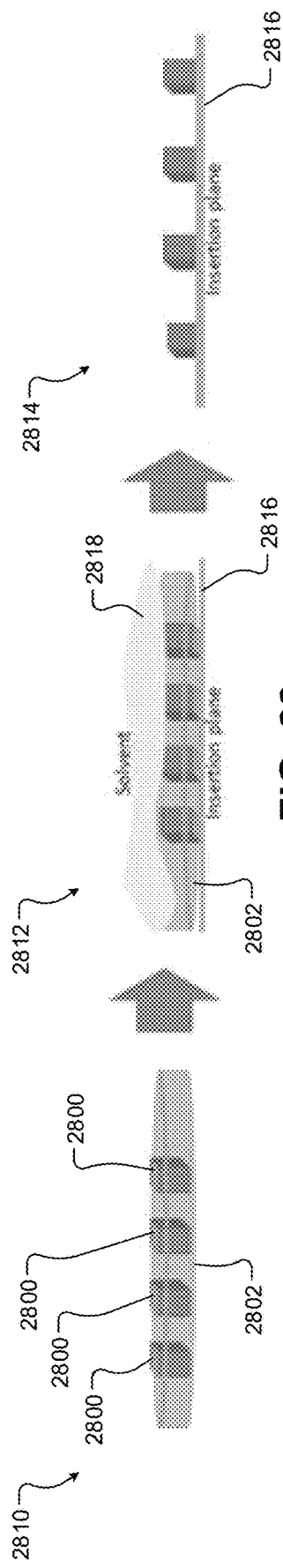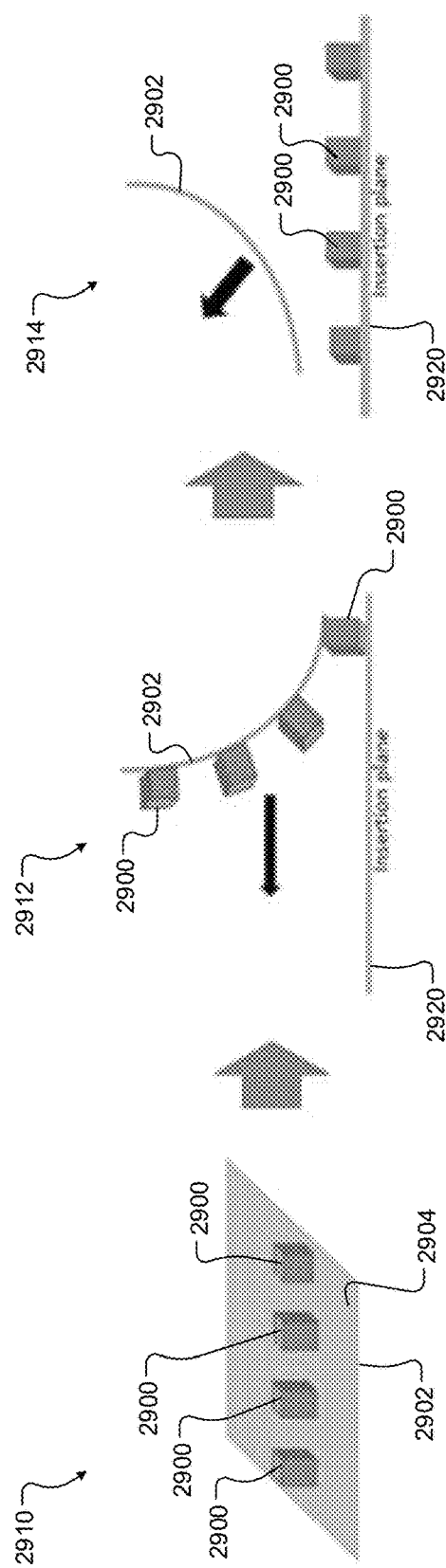

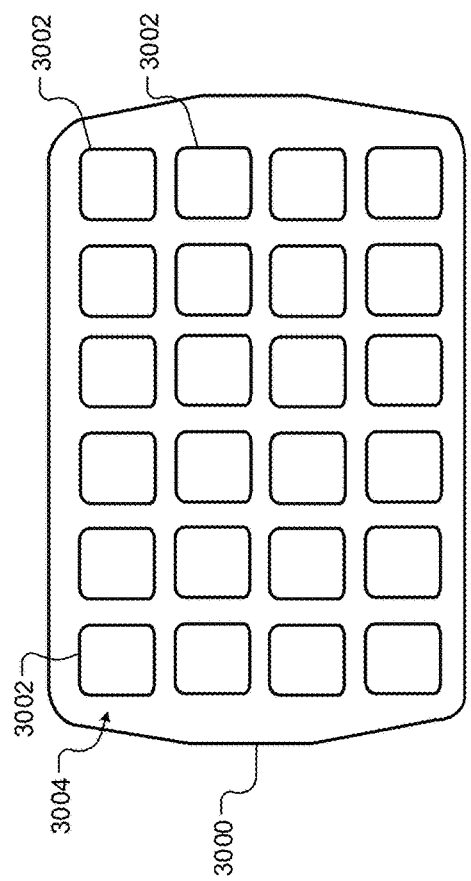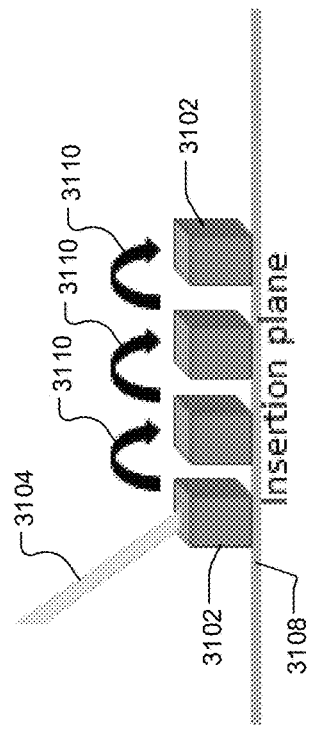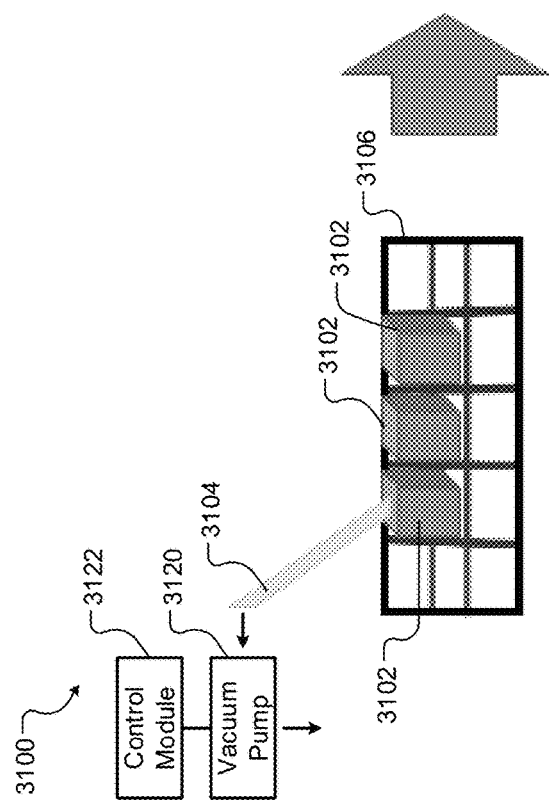
FIG. 30
FIG. 31

WIRELESS NEURAL RECORDING DEVICES AND SYSTEM WITH TWO STAGE RF AND NIR POWER DELIVERY AND PROGRAMMING

CROSS-REFERENCE TO RELATED APPLICATIONS

This application claims the benefit of U.S. Provisional Application No. 62/975,333, filed on Feb. 12, 2020. The entire disclosure of the application referenced above is incorporated herein by reference.

GOVERNMENT CLAUSE

This invention was made with government support under EY029452 awarded by the National Institute of Health. The government has certain rights in the invention.

FIELD

The present disclosure relates to neural recording systems and motor prediction.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Neural recording systems including brain machine interfaces enable motor prediction in paralyzed or severely injured individuals. Motor prediction refers to the ability of a system to determine a desired movement of an individual being monitored by the neural recording system. Motor prediction data can be used, for example, to perform accurate arm and hand control operations. Implantable neural recording systems have historically used wires for data communication and power. This increases risks of tissue damage, infection, and cerebrospinal fluid leakage, rendering these devices unsuitable for long-term implantation.

SUMMARY

A mote is provided and is configured to be implanted within a patient. The mote includes an optical receiver, a control module, a clock generation circuit, a data recovery circuit, a first amplifier, a chip identifier module and a driver. The optical receiver is configured to wirelessly receive a first power and data signal in form of near infrared light energy within the patient and convert the near infrared light energy to an electrical signal having a supply voltage. The control module is configured to power devices of the mote by supplying the supply voltage to the devices. The clock generation circuit is configured to lock onto a target clock frequency based on the first power and data signal and generate clock signals. The data recovery circuit is configured to set parameters of one or more of the devices based on the first power and data signal and a first one of the clock signals. The first amplifier is configured to amplify a neuron signal detected via an electrode inserted in tissue of the patient. The chip identifier module is configured to, based on a second one of the clock signals, generate a recorded data signal, where the recorded data signal is generated based on a chip identifier of the mote and the neuron signal. The driver is configured to transmit the recorded data signal from the mote via a first light emitting diode or a radio frequency transmitter.

In other features, the driver is configured to transmit the recorded data signal from the mote via the first light emitting diode. In other features, the driver is configured to transmit the recorded data signal from the mote via the radio frequency transmitter. In other features, the optical receiver includes a photovoltaic diode configured to convert the near infrared light energy to the electrical signal having the supply voltage.

In other features, the devices include devices of the clock generation circuit and the data recovery circuit. In other features, the mote further includes: the electrode, where the electrode is a carbon fiber; and the first light emitting diode.

In other features, the optical receiver is configured to wirelessly receive the first power and data signal from a repeater and transmit the recorded data signal to the repeater. In other features, the first amplifier is a 3-stage bandpass differential amplifier. In other features, the first amplifier includes a low-nose amplifier, a first voltage gain amplifier and a second voltage gain amplifier.

In other features, the mote further includes: a non-overlap module configured to, based on a third one of the plurality of clock signals, generate phase signals; a current generator configured to, based on the phase signals, generate a current reference; a voltage generator configured to, based on the phase signals, generate a voltage reference; and the first amplifier is configured to amplify the neuron signal based on the current reference and the voltage reference.

In other features, the mote further includes an integration circuit and a comparator. The integration circuit includes: a rectifier configured to generate a rectified signal based on the amplified neuron signal; and an integrator configured to generate an integrated signal based on the rectified signal. The comparator is configured to compare the integrated signal to a voltage threshold and generate a pulsed signal. The chip identifier module is configured to generate the recorded data signal based on the pulsed signal.

In other features, the chip identifier module is configured to encode the recorded data signal based on the chip identifier. In other features, the chip identifier module is configured to generate the recorded data signal using symbol interval modulation.

In other features, the mote further includes a housing. A volume of the housing is smaller than 250 $\mu m^3$. The control module, clock generation circuit, data recovery circuit, first amplifier and chip identifier module are disposed in the housing.

In other features, the housing is 240 $\mu m$ wide with a height of 220 $\mu m$. In other features, the optical receiver is implemented as a photovoltaic cell and the control module is implemented as a chip. Outer top surface dimensions of the photovoltaic cell and the chip are 170 $\mu m \times 190$ $\mu m$.

In other features, the control module includes the clock generation circuit, data recovery circuit, first amplifier and chip identifier module. In other features, a neural recording system includes: the mote of claim 1; and a repeater configured to be implanted in the patient, transmit the first power and data signal in form of near infrared light energy to the mote, and receive the recorded data signal in form of near infrared light energy from the mote.

In other features, the repeater includes: a second light emitting diode configured to emit the first power and data signal; and a photodiode configured to detect near infrared light energy associated with the recorded data signal. In other features, the photodiode is implemented as a single-photon avalanche diode. In other features, the chip identifier module is configured to encode the recorded data signal based on the chip identifier; and the repeater is configured to decode the recorded data signal.

In other features, the neural recording system further includes an external device configured to be disposed external to the patient and transmit a first radio frequency signal to the repeater. The repeater is configured to convert the first radio frequency signal to the first power and data signal, convert the recorded data signal to a second radio frequency signal, and transmit the second radio frequency signal to the external device.

In other features, the repeater is configured to calculate spiking band power corresponding to the neuron signal based on the recorded data signal and/or the external device is configured to calculate the spiking band power corresponding to the neuron signal based on the second radio frequency signal. In other features, the repeater is configured to make motor predictions based on the recorded data signal and/or the external device is configured to make motor predictions based on the second radio frequency signal.

In other features, a neural recording system is provided and includes motes and a repeater. The motes include a first mode and a second mote. The first mote and/or the second mote is configured as an above-described mote. A repeater is configured to: be implanted in the patient; transmit the first power and data signal in form of near infrared light energy to the first mote; receive the recorded data signal in form of near infrared light energy from the first mote; transmit a second power and data signal in form of near infrared light energy to the second mote; and receive a second recorded data signal in form of near infrared light energy from the second mote. The second recorded data signal includes a chip identifier of the second mote.

In other features, the neural recording system further includes an external device configured to be disposed external to the patient and transmit a first radio frequency signal to the repeater. The repeater is configured to: convert the first radio frequency signal to the first power and data signal; covert the first radio frequency signal to the second power and data signal; convert the recorded data signal of the first mote and the second recorded data signal of the second mote to at least one of a second radio frequency signal or a third radio frequency signal; and transmit the at least one of the second radio frequency signal or the third radio frequency signal to the external device. The external device is configured to distinguish data in the at least one of the second radio frequency signal or the third radio frequency signal as being associated with the first mote or the second mote based on at least one of the chip identifier of the first mote, the chip identifier of the second mote or an indication provided by the repeater indicating which portion of the data corresponds to the first mote and which portion of the data corresponds to the second mote.

In other features, a mote insertion method is provided and includes: disposing motes in a dissolvable substance, on a multi-layer material stack, or in a mold, where the motes include an above-described mote; placing the motes at least partially along an insertion plane defined by the tissue of the patient; inserting the electrodes of the motes in the tissue; and either (i) dissolving the dissolvable substance or (ii) removing the multi-layer material stack or the mold from the motes.

In other features, the mote insertion method includes applying a solvent to dissolve the dissolvable substance. In other features, the dissolvable substance includes polyethylene glycol. In other features, the mote insertion method includes peeling the multi-layer material stack or the mold from the motes.

In other features, a mote insertion method is provided and includes: disposing motes in a dissolvable substance, on a multi-layer material stack, or in a mold, where the motes include an above-described mote; and placing the motes at least partially along an insertion plane defined by the tissue of the patient. Placement of the motes includes creating a vacuum on a side of one of the motes to allow lifting and moving of the one of the motes.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 21 is a comparison table of parameters and features of different recording systems including parameters and features for one of the wireless neural recording systems disclosed herein;

FIG. 28 is an insertion diagram illustrating insertion of neural recording motes using a dissolvable substance in accordance with an embodiment of the present disclosure;

FIG. 29 is another insertion diagram illustrating insertion of neural recording motes using a gel pak in accordance with an embodiment of the present disclosure;

FIG. 30 is a top view of a mold for multiple neural recording motes and insertion thereof in accordance with an embodiment of the present disclosure; and FIG. 31 is an insertion diagram illustrating a vacuum pick and place method for insertion of neural recording motes in accordance with an embodiment of the present disclosure.

In the drawings, reference numbers may be reused to identify similar and/or identical elements.

DETAILED DESCRIPTION

Figure 1:
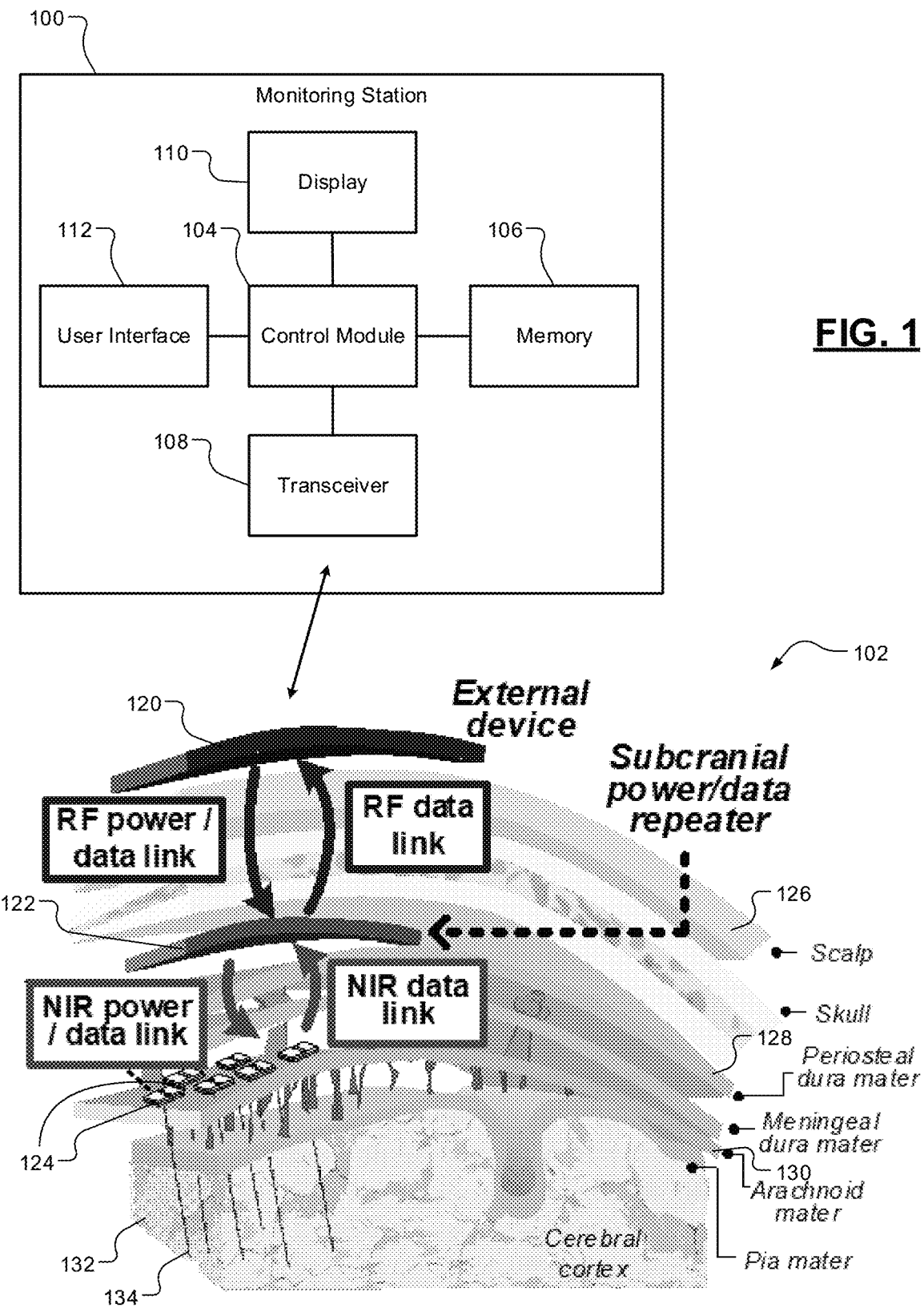
FIG. 1 is a functional block diagram and perspective view of an example monitoring station and an example wireless neural recording system in accordance with an embodiment of the present disclosure.

Several wireless and miniaturized neural recording implants with various power and data transmission methods exist. As an example, an electrocorticography (ECoG) recording system can be used for near-field RF power transfer and bilateral communication. This system has 0.5 watt (W) transmissions, which exceed maximum exposure limits of human tissue by ten times a permissible level. As another example, ultrasonic telemetry may be safely used to send more power than a RF based system. An ultrasonic telemetry system however requires millimeter (mm)-scale implantable device dimensions (e.g., 0.8 mm$^3$) due to bulky ultrasound transducers.

Near infrared (NIR) light may be used to downlink power and data from an external device to an implanted device via a photovoltaic (PV) cell. A data uplink may be provided via a LED at the implantable device and an externally located photodetector. For this type of implementation, implantable device dimensions can be scaled to hundreds of microns (e.g., 0.0297 mm$^2$ neural recording system) using a 50 mW/mm$^2$ light source, which has less than $\frac{1}{6}^{th}$ of the safety power limit for brain tissue. This type of system is however limited to a single light channel and since the system only has a surface electrode, the system is only able to record surface potentials (face-down, potentially blocking the light channel) unless the system is injected into brain tissue. Injecting the system into brain tissue creates significant tissue damage, which can cause bleeding.

The examples set forth herein include a repeater and implantable motes that wirelessly receive power and transfer data using RF and NIR links. As an example, the repeater may have a cross-section that is 2 centimeters (cm$^2$) and the motes may be a 0.74 μW integrated circuit (IC) having a cross-section that is 0.19×0.17 mm$^2$. As another example, each of the motes is 240 μm×240 μm×220 μm and used as a wireless neural recording probe. The repeater is configured to determine "spiking band power (SBP)" on-chip to save 920 times the amount of power typically used while maintaining accurate human finger position and velocity decoding. SBP refers to an absolute average of signal amplitude in the 300-1000 Hz band in 10-50 MS windows is dominated by large single units rather than high frequency local field potential (LFP). Using this band and windows for decoding allows for finger movement prediction without accuracy degradation. SBP drops the signal bandwidth to 1 kHz, which significantly reduces amplifier power and reduces communication bandwidth to 100 Hz further reducing system power.

The motes are wireless neural recording ICs for motor prediction with NIR based power and data telemetry. The motes are designed for a larger neural recording system in which numerous motes (also referred to as micro-probes) are disposed in the brain in a sub-dural space. The motes record neural spikes using carbon fiber electrodes that penetrate several millimeters into brain tissue. The carbon fiber electrodes have been shown to incur minimal chronic scar formation. The motes are powered and globally programmed by, for example, 850 nm NIR light emitted from a repeater placed in the epidural space of the brain and received at the motes. LEDs on the motes are used as part of data uplinks. The light emitted by the LEDs is received by the repeater using, for example, single-photon avalanche diodes (SPADs). As an example, the repeater may service hundreds of motes, which are each distinguished by respective on-chip IDs and locations. The repeater is larger than the motes and uses an RF (or inductive) link for wireless power and data communication with an external receiver.

Figure 6:
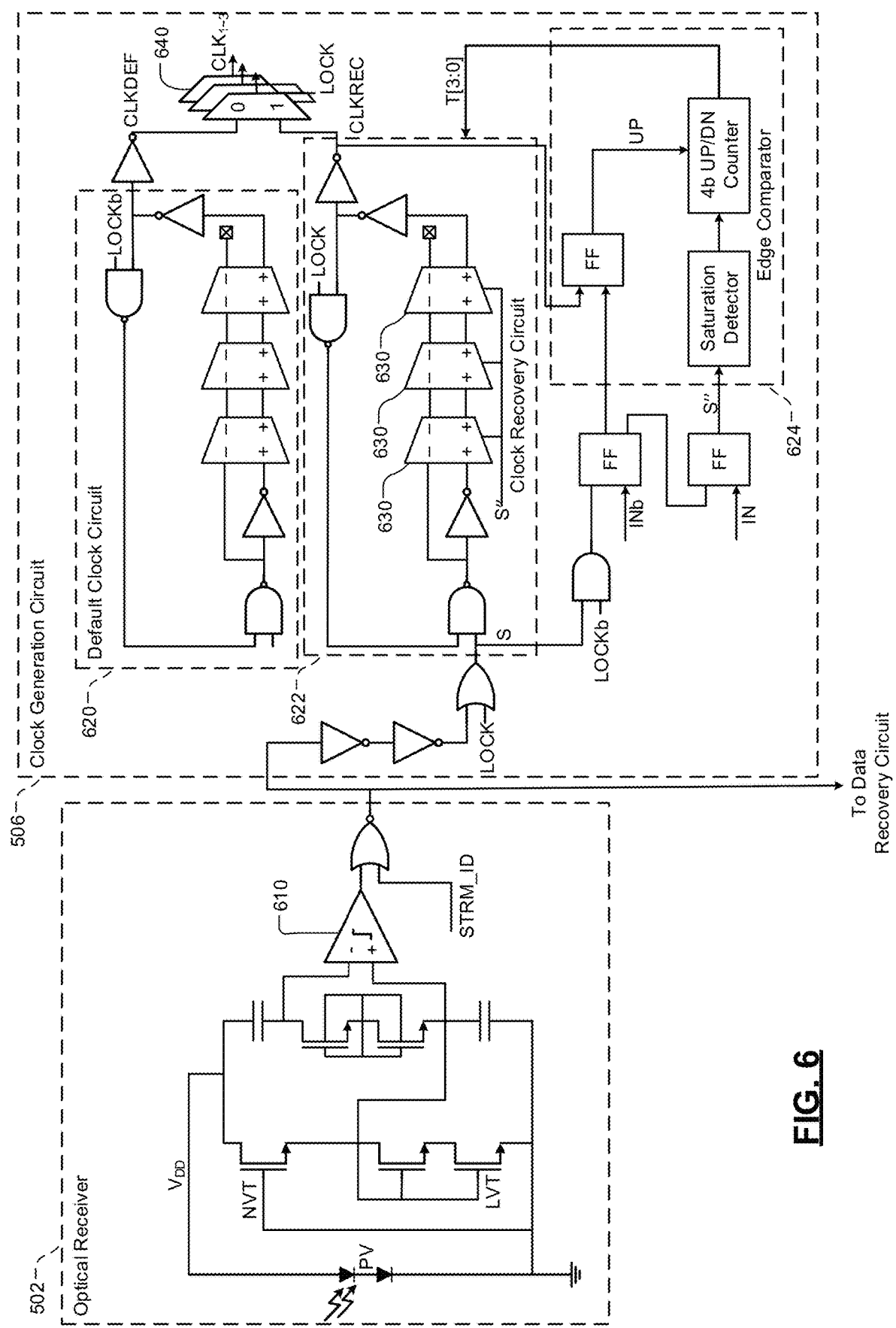
FIG. 6 is a schematic view of an optical receiver and a clock generation circuit of the mote of FIG. 5 in accordance with an embodiment of the present disclosure.
Figure 11:
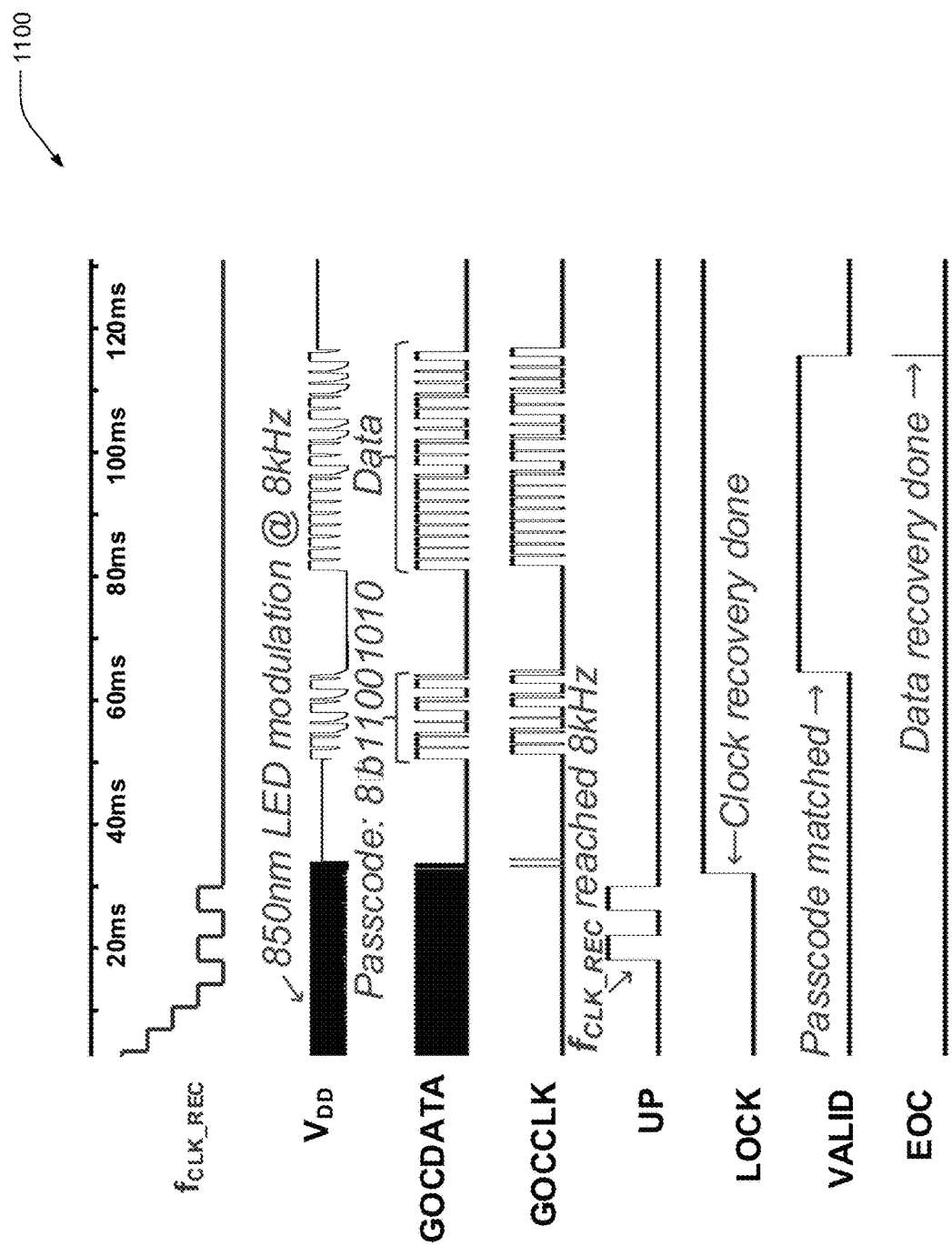
FIG. 11 is an example signal diagram during clock and data recovery in accordance with an embodiment of the present disclosure.

In one embodiment, the motes are complementary metal-oxide-semiconductor (CMOS) ICs that include optical receivers followed by clock and data recovery circuits, a random-number chip ID module, a neural recording amplifier (referred to below as a 3-stage bandpass differential amplifier), a rectifier based integrator (or SBP extractor) module, and a LED driver. An example of the optical receiver and corresponding measured signal diagram are shown in FIGS. 6 and 11. Supply power voltage $V_{DD}$ is AC-coupled to a comparator input to convert modulated light from the repeater to a digital signal. The comparator may have a hysteresis (e.g., 80 mV hysteresis) to remove glitches due to unwanted $V_{DD}$ fluctuations. In a power-on reset phase, the clock recovery circuit locks the on-chip recovery clock to a precise predetermined (e.g., 8 kHz)

modulated light from the repeater. The recovered clock is used to set a reference current, which is precisely controlled for reliable amplification and signal filtering.

The clock recovery circuit searches a digitally-controlled oscillator (DCO) thermometer-coded configurations to match a received modulation period with a DCO period. The clock recovery circuit then switches the system clock from a default to a recovery clock using glitch-free multiplexers. After clock locking, the repeater programs the mote by transmitting a downlink signal in the form of pulse width modulated (PWM) light. In an embodiment, an 8 bit hard-wired passcode is implemented to prevent unwanted programming. The signal diagram of FIG. 11 includes plots of signals measured from one of the motes. In one embodiment, the mote is wire-bonded with a dual-junction GaAs photovoltaic (PV) cell that generates 893 nanoamperes (nA) of current $I_{SC}$ at 1.67 volts (V) $V_{OC}$ under 120.5 µW/mm² 850 nanometer (nm) wavelength light.

Figure 5:
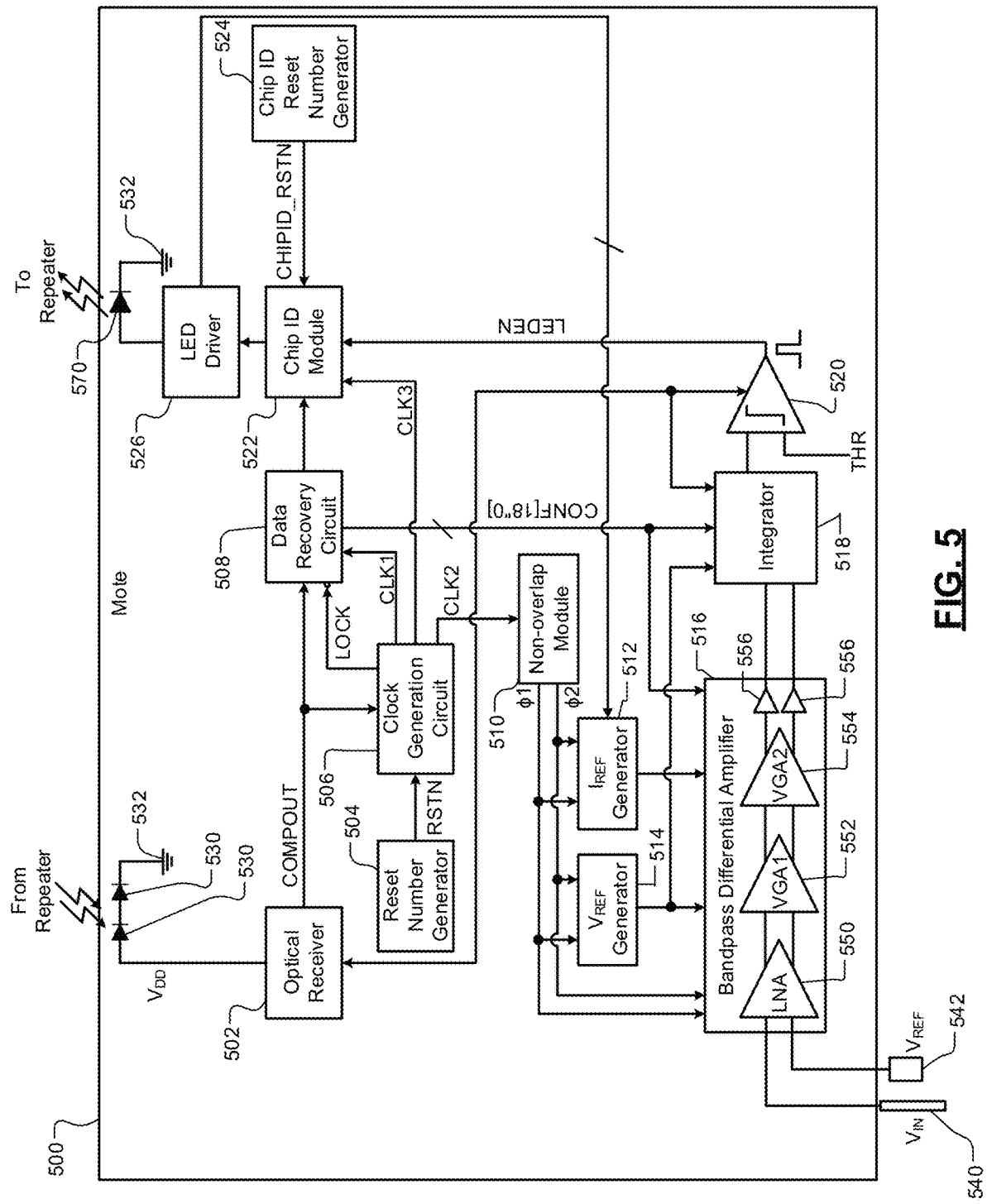
FIG. 5 a functional block diagram of an example of a mote in accordance with an embodiment of the present disclosure.
Figure 12:
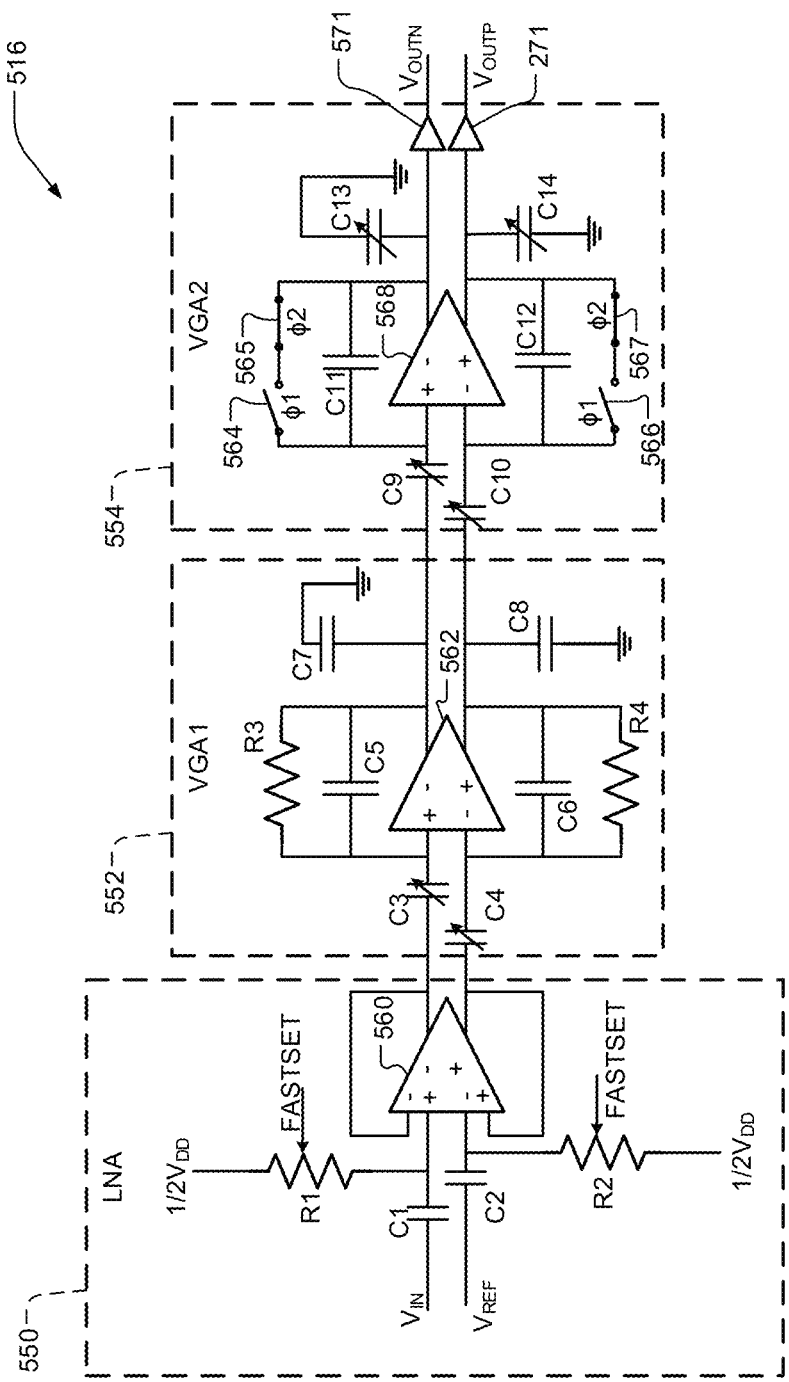
FIG. 12 is a schematic view of a 3-stage bandpass differential amplifier of the mote of FIG. 5 in accordance with an embodiment of the present disclosure.
Figure 14:
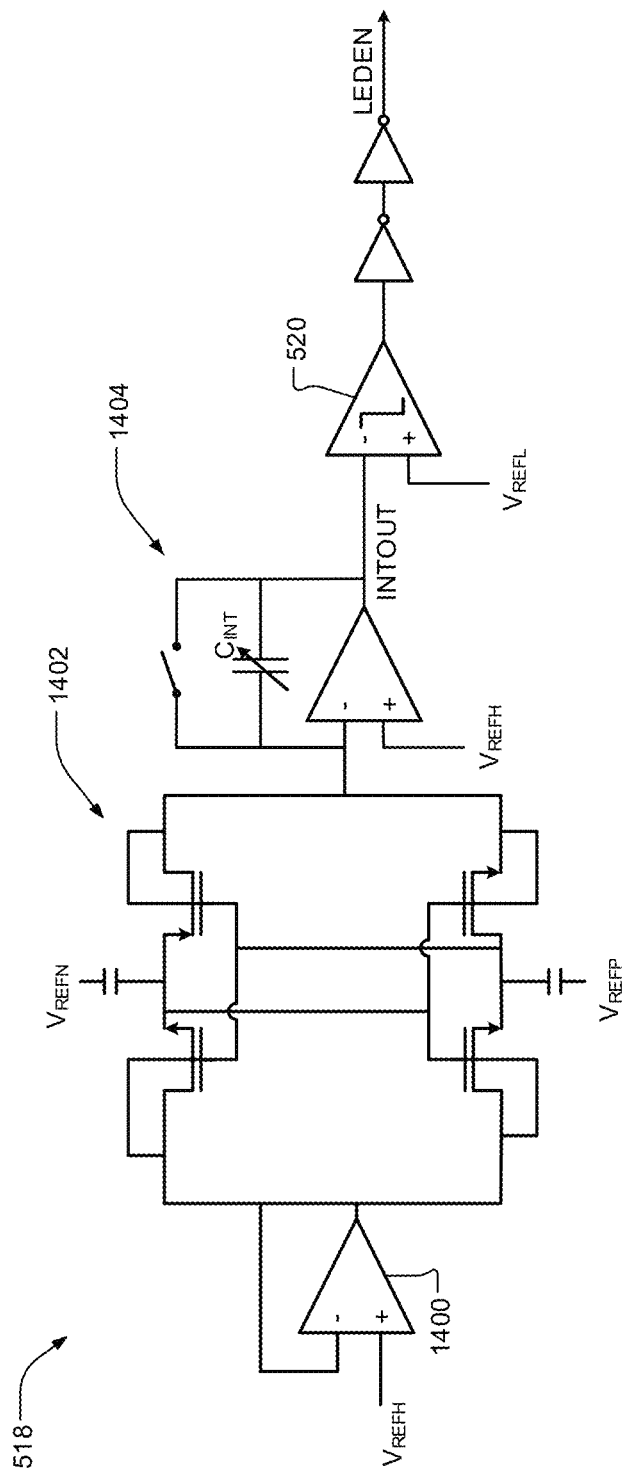
FIG. 14 is a schematic view of an example of a rectifier-based analog integrator of the mote of FIG. 5 in accordance with an embodiment of the present disclosure.

An analog front end (AFE) of the mote supports SBP based finger position and velocity decoding. When used as an input to a trained linear decoding filter, SBP is used to maintain finger position and velocity decoding accuracy relative to a standard 7.5 kHz bandwidth neural recording while reducing the required communication bandwidth from probe to repeater to hundreds of Hz, thereby reducing uplink power. The AFE includes a three-stage bandpass differential amplifier with subsequent source follower and rectifier-based integrator to quantize the SBP. The three-stage bandpass differential amplifier and the rectifier-based integrator are shown in FIGS. 5, 12 and 14.

The three-stage bandpass differential amplifier (or amplifier) includes a low noise amplifier (LNA) and two voltage gain amplifiers (VGAs). In an embodiment, the LNA has a 60 mega-ohm (MΩ) input impedance when receiving a 1 kilo-hertz (kHz) signal, is fully differential and achieves 30 decibels (dB) of gain without use of bulky capacitors. The LNA has a gain $g_m$. The VGAs set a high-cut-off frequency $f_H$ (e.g., 950 Hz) and a low-cut-off frequency $f_L$ (e.g., 180 Hz) and define a spiking band. The high-cut-off frequency $f_H$ is set by a bias current of the second VGA, which is generated based on a current reference. The current reference is generated based on a voltage reference and output of a switched capacitor operating at a clock frequency $f_{CLK}$. The low-cut-off frequency $f_L$ is defined by a direct current (DC) servo loop of the second VGA, which has a feedback impedance defined by $1/C_{SW}f_{CLK}$, where $C_{SW}$ is the capacitance of the switched capacitor. The DC servo loop refers to a high impedance feedback loop. High impedance feedback loops are provided by capacitors C11 and C12. Accuracy of $f_H$ and $f_L$ is ensured by locking $f_{CLK}$ during clock recovery to a clock of the repeater. As an example, peak gain may be measured at 69 dB while amplifying action potential (AP) spikes in 180-950 Hz bandwidth for SBP-based motor prediction. As another example, measured input-referred noise (IRN) may be 4.8 µV root mean square (rms) while consuming 510 nW at 38° C.

Figure 17:
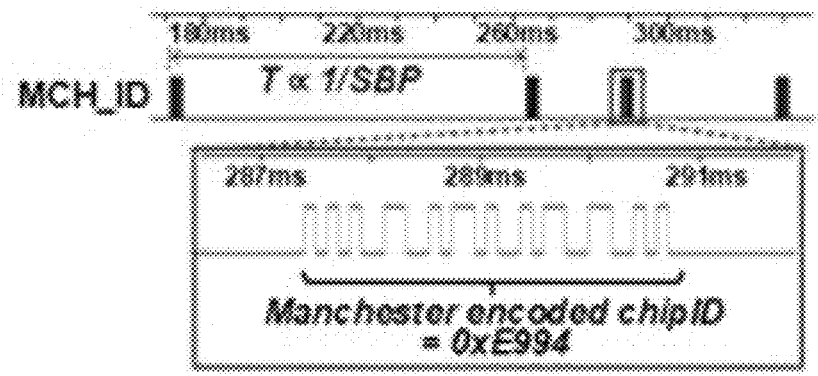
FIG. 17 is an example diagram of a Manchester encoded chip identifier (ID) in accordance with an embodiment of the present disclosure.

The 3-stage bandpass differential amplifier drives the rectifier-based integrator, which has an output initially pre-charged to $V_{REFH}$. An output of a rectifier of the rectifier-based integrator decays at a rate proportional to an amplitude at an input of the rectifier. When the output of the rectifier drops below $V_{REFL}$, a pulse is generated and provided as an integrator output signal LEDEN. The output signal LEDEN triggers an LED driver of the mote to transmit a unique chip ID (e.g., Manchester encoded (unique) chipID) of the mote. This transmission consumes 6.7 pico-joules per bit (pJ/b) (post layout simulation). An example of the unique chip ID is shown in FIG. 17. As a result, a LED output firing rate or frequency of the mote is proportional to the SBP.

Figure 16:
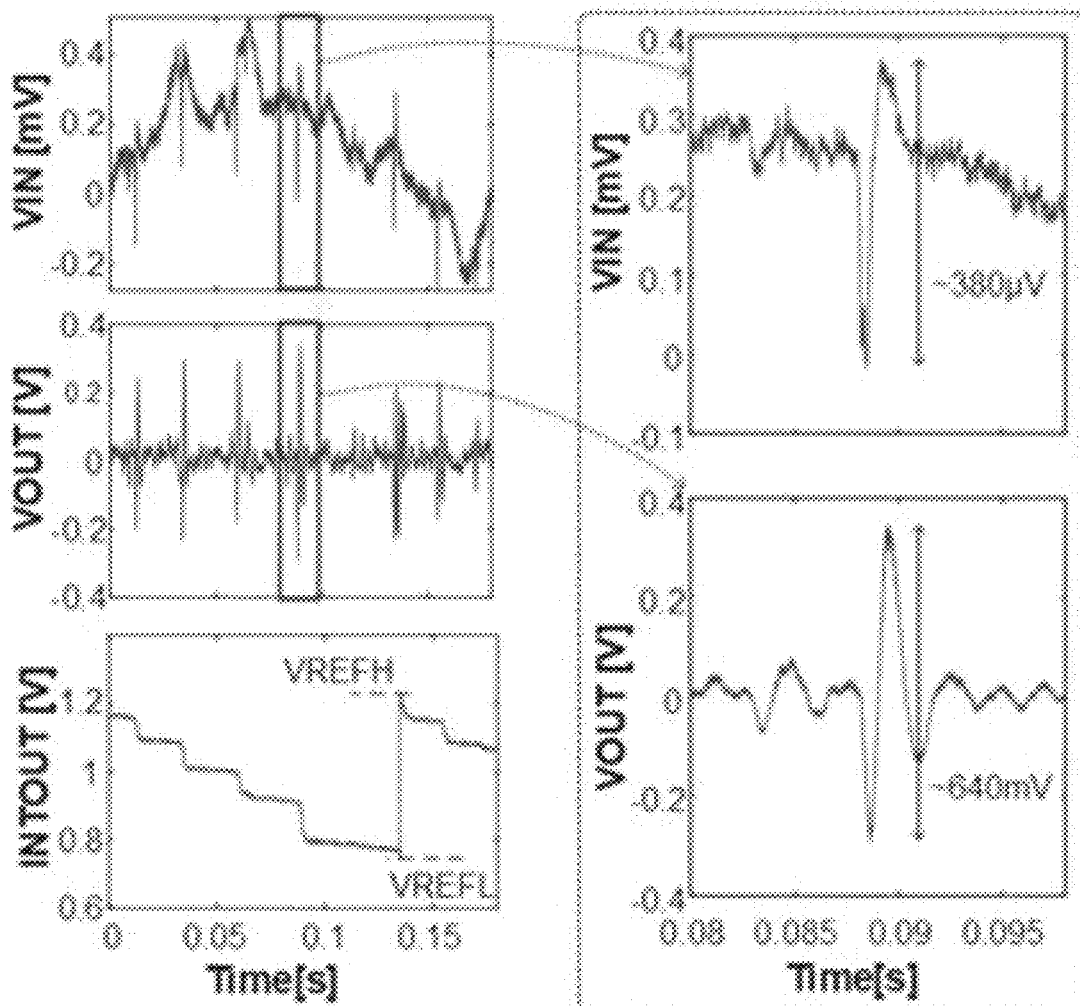
FIG. 16 is an example diagram of in vivo transient measurement results in accordance with an embodiment of the present disclosure.

The functionality of the AFE functionality has been verified in vivo using a carbon fiber driven ~1.3 mm into a motor cortex of an anesthetized Long Evans rat. A commercial recording system (24.414 kilo symbols per second (kSps), with a bandwidth between 2.2 Hz and 7.5 kHz) connected to the carbon fiber electrode in parallel to the IC is used for an accuracy comparison. All procedures complied with the Institutional Animal Care and Use Committee. VIN is an input voltage of the amplifier, which may be measured by the commercial recording system. VOUT (VOUT$_P$–VOUT$_N$) is a measured output voltage of the amplifier. Results show that an output INTOUT of the rectifier-based integrator steps down at each motor cortex neuron spike and is restored to $V_{REFH}$ when the output INTOUT reaches $V_{REFL}$. This is shown in FIG. 16.

Figure 18:
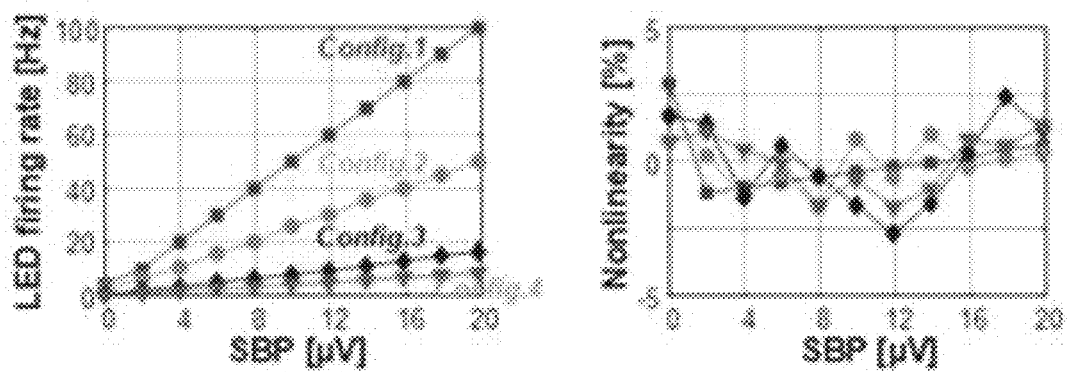
FIG. 18 is an example diagram of neural simulation plots in accordance with an embodiment of the present disclosure.

The LED output firing rate linearity across SBP of the mote has been tested using synthesized AP spikes (e.g., 240 µV peak-to-peak with 1 ms width) at varying rates from 0 to 100 Hz. This is shown in FIG. 18. In an embodiment, the measured LED output firing rate is proportional to SBP with nonlinearity <±2.9% and has sensitivity programmable from 0.4 to 5.0 firings per µV. Overall functionality has been verified using three different types of input signals; a synthesized neural simulator input signal, an in vivo rat motor cortex input signal, and a pre-recorded monkey motor cortex input signal. See FIGS. 19A-19B.

Figure 20:
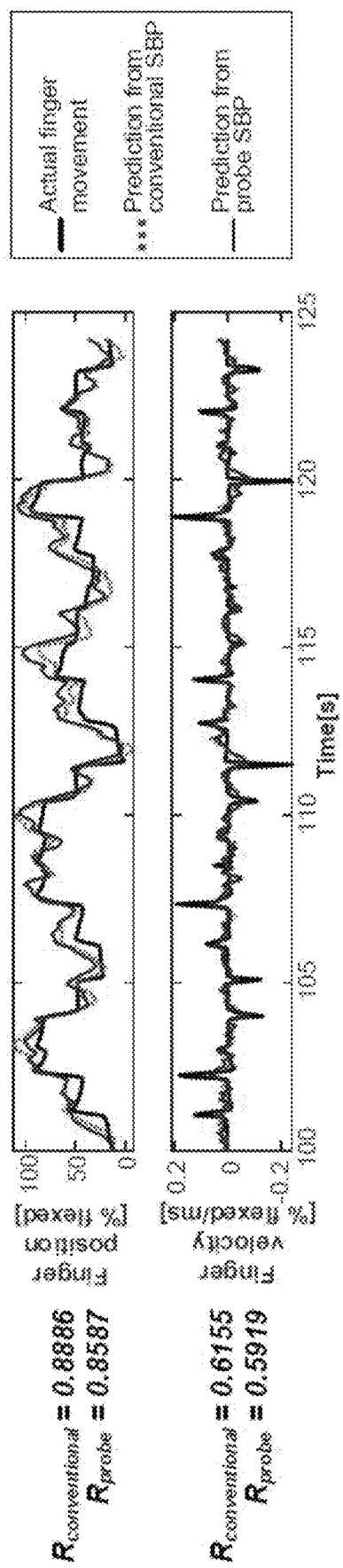
FIG. 20 is an example diagram of a finger position/velocity decoding result in accordance with an embodiment of the present disclosure.
Figure 22:
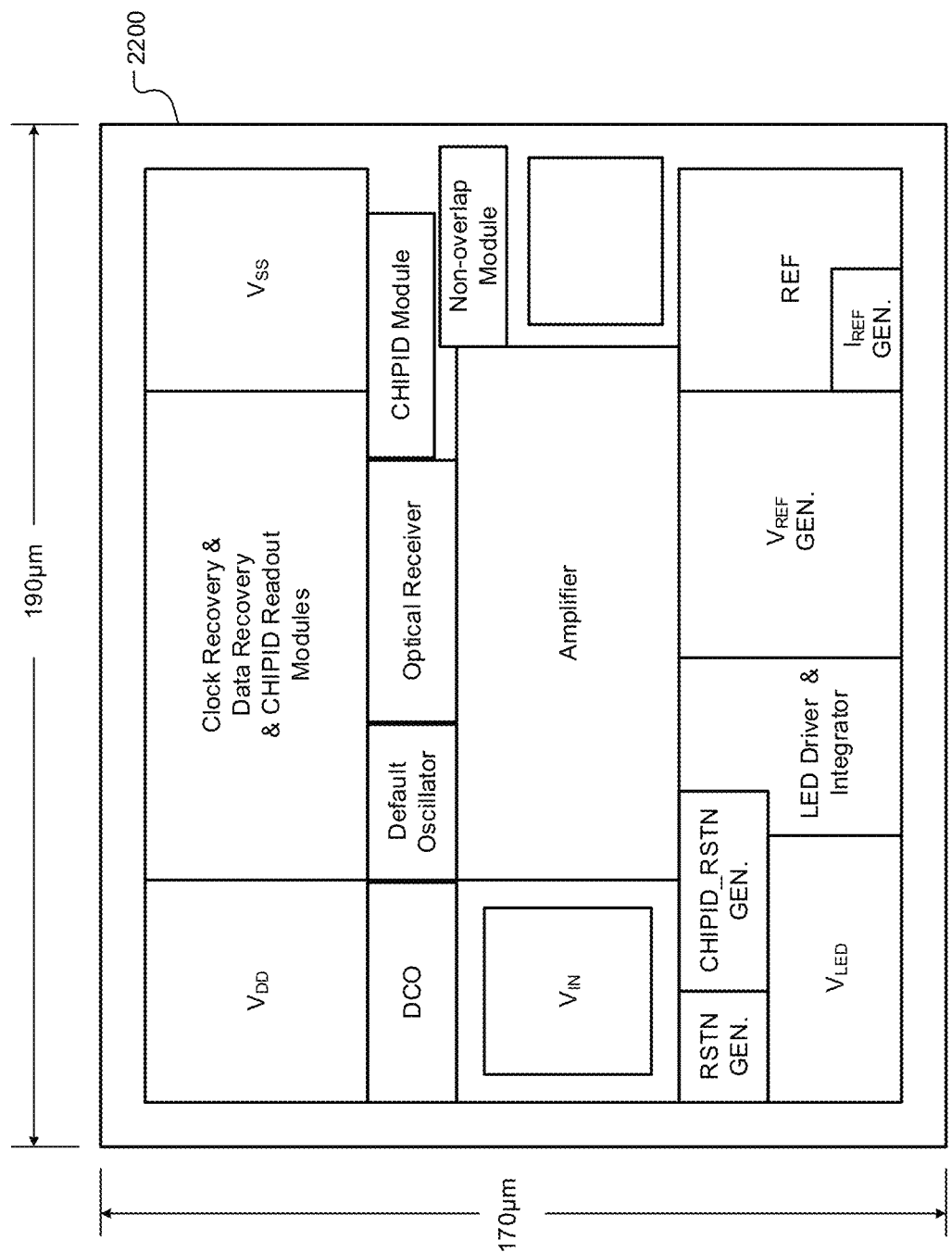
FIG. 22 is an example chip layout of a mote in accordance with an embodiment of the present disclosure.

SBP of the mote (or measured probe SBP) is decoded from a measured time interval of the LEDEN signal and compared with a result generated by a conventional high-power AFE using a digital signal processing SBP calculation. The measured probe SBP accurately matches the conventional system results. See, for example, FIG. 20. FIG. 20 shows finger position and velocity decoding results using a Kalman-filter with conventional and probe SBP results using pre-recorded 20-channel neural signals of a male monkey. Position Kalman filter training/prediction may be performed, an example of which is described in Z. T. Irwin, et. al., "Neural control of finger movement via intracortical brain-machine interface," *J. Neural Engineering*, vol. 14, no. 6, p. 066004, December 2017. All procedures complied with the Institutional Animal Care and Use Committee. An embodiment of the disclosed system accurately predicts finger position and velocity with a state-of-the-art correlation coefficient of 0.8587 for position and 0.5919 for velocity while a conventional high-power and wired system demonstrates a correlation coefficient 0.8886 for position and 0.6155 for velocity. In one embodiment, the IC of the mote is fabricated as a 180 nm CMOS chip, an example layout of which is shown in FIG. 22. The table shown in FIG. 21 provides a comparison to previously published wireless neural probe chip designs. In an embodiment, the mote is able to consume 0.74 µW with 3.76 amplifier noise efficiency factor (NEF) with a 1.5 V power supply at 38° C., achieving best noise performance among comparable designs.

Although examples are shown and described for monitoring brain neuron activity, the neural recording systems disclosed herein are applicable for recording neuron activity in any tissue, for recording any electrical signal in a body, and/or for other bioelectrical applications. The neural recording systems may be used for various motor applications, brain interface applications, spinal cord injury applications, etc. The neural recording systems may be used on patients with epilepsy and to determine when to stimulate tissue, such as for closed loop deep brain stimulation. The disclosed systems eliminate the need for large wired electrodes used in previous recording systems. The neural recording systems may be used for diagnosis determinations and for seizure detection purposes. The neural recording systems provide the stated recording using devices that are less than 1 mm³ using highly biocompatible electrodes and provide safe recording through a skull of a patient. The only items implanted in, for example, brain tissue and/or other monitored tissue are the electrodes, which in an embodiment, are carbon fibers.

FIG. 1 shows a monitoring station 100 and an example wireless neural recording system 102. The monitoring station 100 may be a computer, a server, or other monitoring station that communicates with the wireless neural recording system 102. The monitoring station 100 may include a control module 104, a memory 106, a transceiver 108, and a display 110 and/or another user interface 112. The control module 104 may transmit control signals to and receive data from the wireless neural recording system 102 via the transceiver 108.

The wireless neural recording system 102 includes an external device 120, a repeater 122, and multiple motes (or neural probes) 124. The external device 120 is disposed on and outside of a scalp 126 of a patient. The repeater 122 may be, for example, implanted and disposed in periosteal dura mater 128. The motes 124 may be, for example, implanted and disposed on arachnoid mater 130. Any number of motes may be implanted. In one embodiment, hundreds of motes are implanted. Each of the motes 124 has an electrode (e.g., a carbon fiber electrode) that extends from that mote and into a cerebral cortex 132. One of the electrodes is designated 134.

During operation, the external device 120, which has a power source (e.g., a battery), generates a radio frequency (RF) power and data downlink signal, which is transmitted to the repeater 122. This provides power to the repeater 122 and data to program the motes 124. The repeater 122 then generates NIR power and data downlink signals, which are transmitted respectively to the motes 124 to provide power to and program the motes 124. The motes 124, once programmed, generate recorded data signals, which are transmitted via NIR data uplinks back to the repeater 122. The repeater 122 then forwards the received data and/or other generated data in the form of a RF uplink signal to the external device 120. The external device 120 then, based on the data, makes motor predictions. This process is referred to as a two-stage RF/NIR approach for recording and transmitting neural signals.

Figure 2:
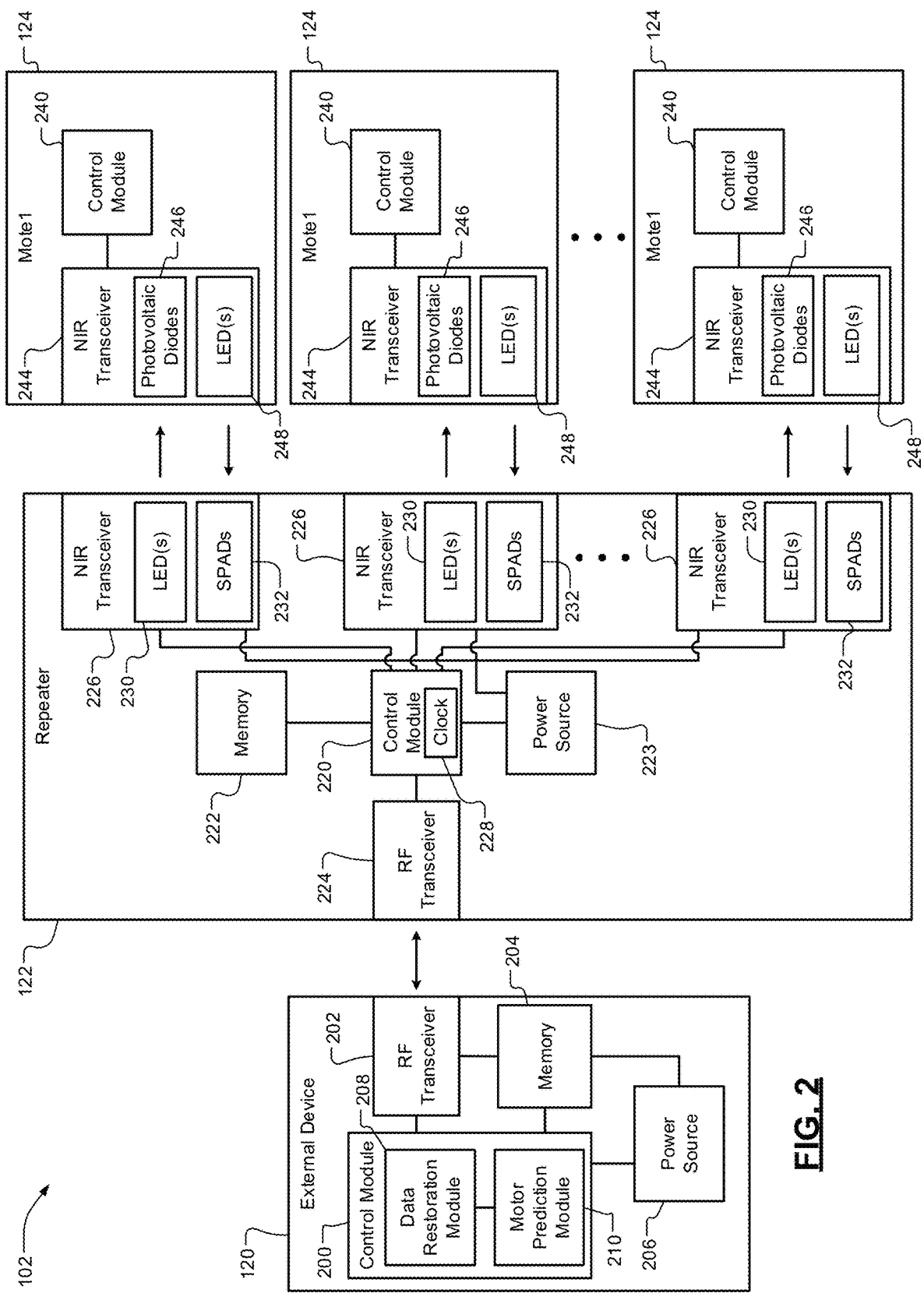
FIG. 2 is a functional block diagram of an example of the wireless neural recording system of FIG. 1.

FIG. 2 shows the wireless neural recording system 102 including the external device 120, the repeater 122 and the motes 124. The external device 120 may include a control module 200, a RF transceiver 202 and a memory 204, which may be powered by a power source (e.g., a battery) 206. The control module 200 may include a data restoration module 208 and a motor prediction module 210. The restoration module 208 may recover data received from the repeater 122. The motor prediction module 210 makes motor predictions based on the recovered data and perform one or more actions based on the motor predictions.

The repeater 122 includes a control module 220, a memory 222, a power source 223, a RF transceiver 224 and NIR transceivers 226, which communicate respectively with the motes 124. As an example, the repeater may be implemented in a titanium package and the power source 223 may be implemented as a battery. The power source 223 is charged based on power received from the external device 120 via the RF transceiver 224 and supplies power to the control module 220 and the NIR transceivers 226. The RF transceiver 224 communicates with the RF transceiver 202 of the external device 120. The control module 220 includes an internal clock 228. Each of the NIR transceivers 226 includes LEDs 230 and photodiodes 232. The NIR transceivers 226 provide optical communication with the motes 124.

Figure 3:
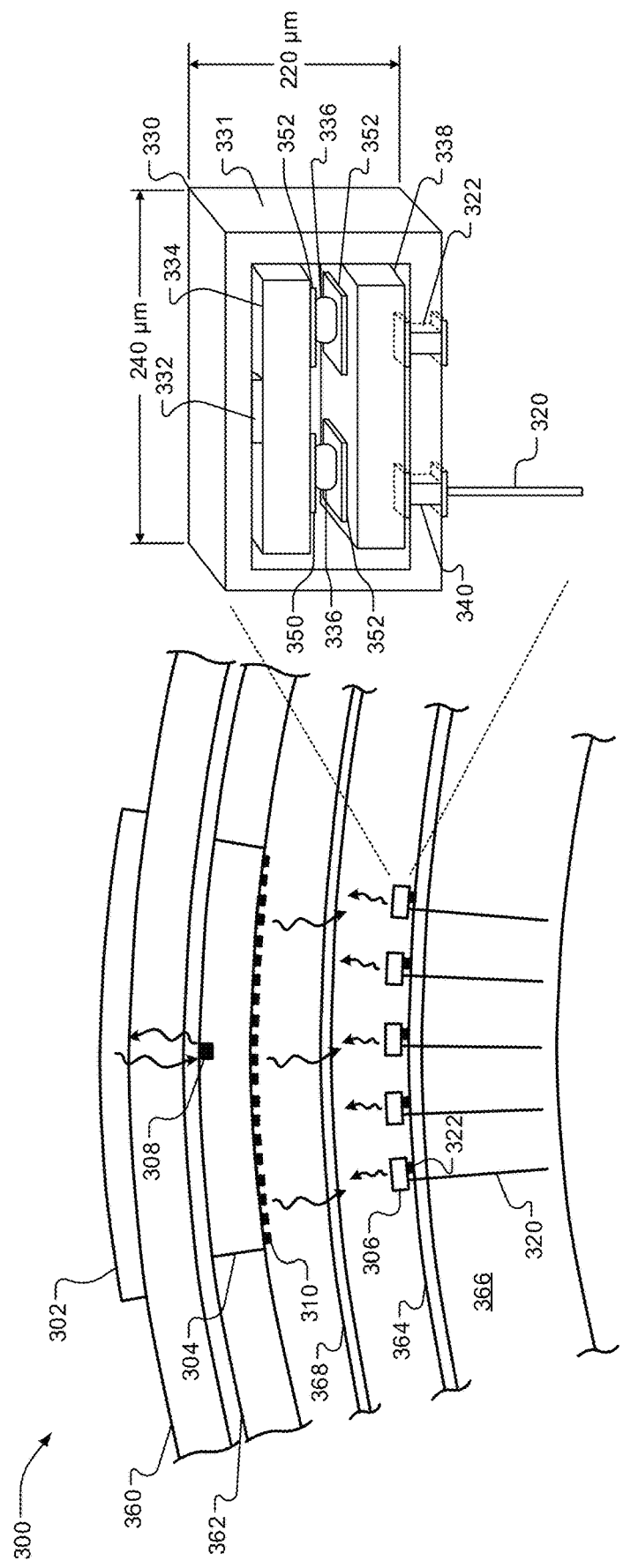
FIG. 3 is a cross-sectional view of the wireless neural recording system including a cross-sectional view of an example of a mote performing near infrared communication in accordance with an embodiment of the present disclosure.
Figure 4:
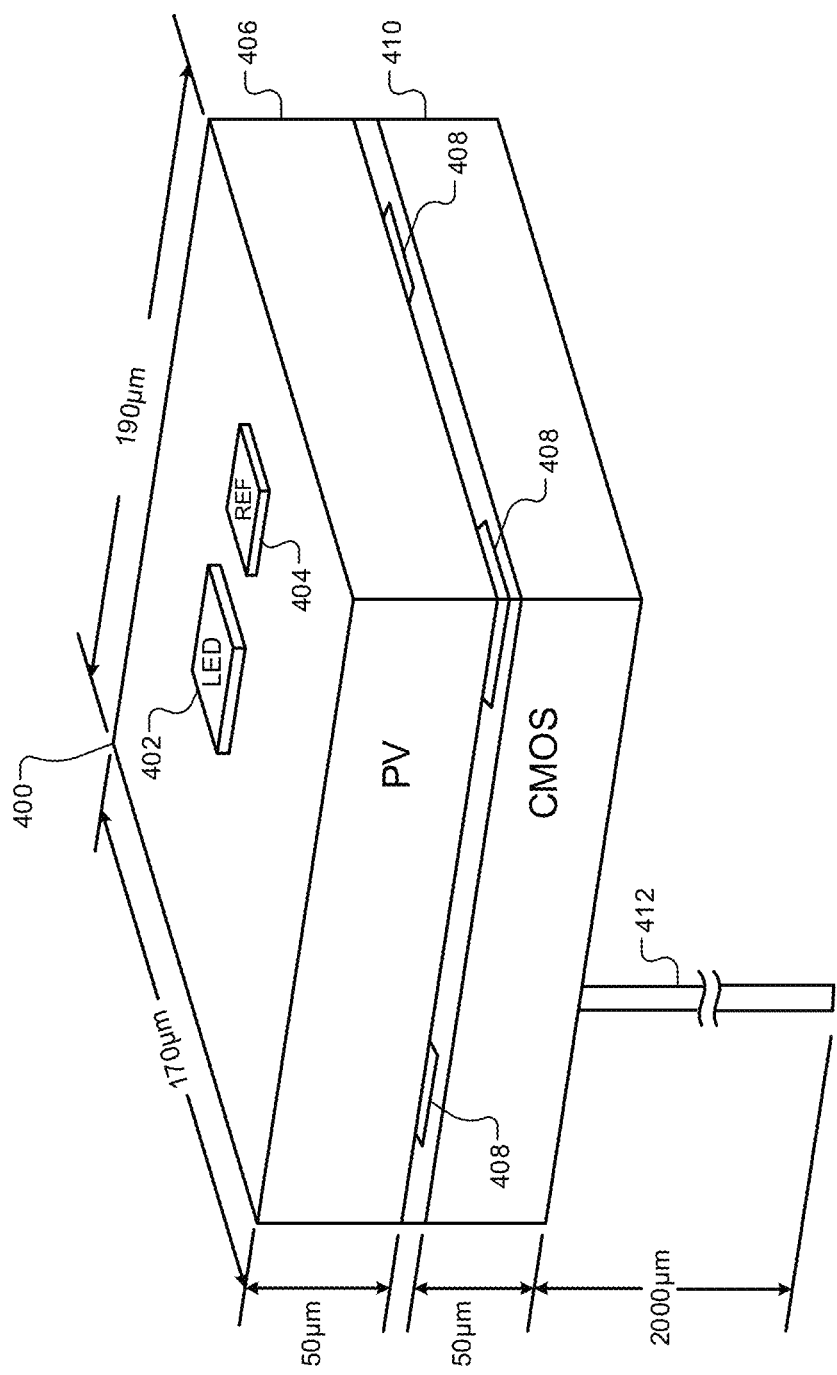
FIG. 4 is a perspective view of an example of a mote in accordance with an embodiment of the present disclosure.

Each of the motes 124 includes a control module 240 and NIR transceivers 244. The NIR transceivers 244 include photodiodes 246 and LEDs 248, which communicate with the LEDs 230 and photodiodes 232 of the NIR transceivers 226 of the repeater 122. In one embodiment, the photodiodes 232 are implemented as single-photon avalanche diodes (SPADs) as shown or as photovoltaic diodes and are part of optical receivers of the NIR transceivers 226 of the repeater 122. Additional examples of the motes 124 are shown in FIGS. 3-5. Each of the control modules 240 may include some or all of the receiver, generators, modules, driver, amplifiers, integrator, comparators and/or other devices shown in the example mote of FIG. 5.

In an embodiment, the repeater 122 provides power to and programs hundreds of motes. Power is provided via the LEDs 230. The photodiodes 246 may be implemented as photovoltaic diodes as shown and perform as power sources for the motes 124 and convert light received from the LEDs 230 to a supply voltage $V_{DD}$. The supply voltage $V_{DD}$ is a DC voltage when simply providing power and is a modulated signal during programming. The programming includes locking a frequency of clock (or oscillator) of each of the motes to a frequency of the clock 228. This synchronization of the motes to the repeater allows signals from the motes to be compared and analyzed relative to each other in time. The programming further includes setting values of devices in the motes 124 and is accomplished by pulse width modulating the light emitted from the LEDs 230. This may include controlling configurations of some or all analog circuit devices of the motes 124 including setting parameters, such as gains of amplifiers of the motes 124. The LEDs 230 provide DC light when in a nominal state to generate a supply voltage $V_{DD}$ of, for example, 1.6V. The control module 220 may perform on-chip signal processing to reduce data bandwidth and increase the number of motes connected to the repeater 122.

FIG. 3 shows another example wireless neural recording system 300 that includes an external device 302, a repeater 304 and motes 306. The wireless neural recording system 300 may replace and/or operate similar to other neural recording systems disclosed herein. The repeater 304 includes an RF transceiver 308 and NIR transceivers 310. The motes 306 include electrodes (e.g., carbon fibers) 320 and reference terminals 322. A cross-sectional perspective view of one of the motes 330 is shown. The mote 330, as with the other ones of the motes 306, may include a housing 331, a LED 332, a photovoltaic (PV) cell 334, bonding balls 336, a chip (e.g., a CMOS chip) 338, a voltage input terminal 340 connected to one of the electrodes 320, and one of the reference terminal 322 (one of the reference terminals 322). The bonding balls 336 are connected to terminals 350, 352 of the PV cell 334 and the chip 338. As an example, the chip 338 may implement one of the control modules 240 of FIG. 2 and optionally a portion of the corresponding one of the NIR transceivers 244. The external device 302 is disposed on a scalp 360. The repeater is disposed in a skull 362.

The motes 306 are disposed on a pia mater 364 above a cerebral cortex 366 and below dura mater 368. The reference terminals 322 are in contact with the pia mater 364 and provide a reference voltage potential. In an embodiment, the motes 306 are floating on top of brain tissue. The motes 306 are μm-scaled and each include a respective carbon fiber and circuit. Photovoltaic diodes of the motes 306 collect light energy provided by the repeater 304 and convert the light energy to electrical energy to power devices of the motes 306. The carbon fibers penetrate tissue to detect electrical potentials of the tissue. The motes 306 acquire neural signals in the tissue using ultra-low power analog front ends, as further describe below. As an example, each of the motes 306 may be 240 μm wide with a height of 220 μm, as shown. In one embodiment, a volume of the housing is less than 250 μm$^3$.

FIG. 4 shows an example mote 400 that includes a LED 402, a reference terminal 404, a PV cell 406, terminals 408, a chip 410 and an electrode (e.g., carbon fiber 412). The reference terminal 404 may provide a reference voltage similar to the reference terminal 322 of FIG. 3, but instead of contacting pia mater, the reference terminal 404 is a floating reference to an area between the pia mater and dura mater. In an embodiment, the example mote 400 is 170 micrometers (μm)×190 μm×100-150 μm and has a carbon fiber that is 2000 μm in length. In another embodiment, the PV cell 406 and the chip 410 are implemented in a housing, a similar example of which is shown in FIG. 3. The chip 410 may be a CMOS chip. As an example, the chip 338 may implement one of the control modules 240 of FIG. 2 and optionally a portion of the corresponding one of the NIR transceivers 244. As another example, the carbon fiber may be attached to the chip 410 using silver epoxy. The carbon fiber is smaller than a neuron, but strong enough to be inserted in tissue and is biocompatible.

FIG. 5 shows an example of a mote 500, which may replace any other mote disclosed herein. The mote 500 includes an optical receiver 502, a reset number generator 504, a clock generation circuit 506, a data recovery circuit 508, a non-overlap module 510, a current generator 512, a voltage generator 514, a 3-stage bandpass differential amplifier 516, a rectifier-based analog integrator 518, a comparator 520, a chip ID module 522, a chip ID reset number generator 524 and a LED driver 526. The clock generation circuit 506, data recovery circuit 508, non-overlap module 510, and chip ID module 522 may be referred to as digital blocks. The optical receiver 502, reset number generator 504, current generator 512, voltage generator 514, 3-stage bandpass differential amplifier 516, rectifier-based analog integrator 518, comparator 520, chip ID reset number generator 524 and LED driver 526 may be referred to as analog blocks.

Examples of the optical receiver 502 and the clock generation circuit 506 are shown in FIG. 6. The optical receiver 502 receives an output of photovoltaic diodes 530, which are connected to a reference terminal 532 that is at a voltage potential $V_{SS}$. The photovoltaic diodes 530 provide the supply voltage $V_{DD}$. Based on the supply voltage and modulation of the output of the photovoltaic diodes 530, the optical receiver generates an output signal COMPOUT, which is provided to the clock generation circuit 506 and the data recovery circuit 508. The supply voltage $V_{DD}$ is provided to the reset number generator 504, the clock generation circuit 506, the data recovery circuit 508, the non-overlap module 510, the current generator 512, the voltage generator 514, the 3-stage bandpass differential amplifier 516, the rectifier-based analog integrator 518, the comparator 520, the chip ID module 522, the chip ID reset number generator 524 and the LED driver 526. The signal COM POUT is modulated during programming of the mote 500, but is at a steady-state during detection of signals via electrode 540 (referred to as the "neuron signal detection mode"). Programming includes clock recovery and data recovery. A constant DC voltage is provided during the neuron signal detection mode.

Referring now to FIG. 6, which shows the optical receiver 502 and the clock generation circuit 506. The optical receiver 502 receives and converts a PWM signal at PV diodes to the digital signal COMPOUT and includes normal voltage threshold (NVT) and low voltage threshold (LVT) N-type metal-oxide-semiconductor (NMOS) transistors, which are used as a voltage divider to provide a reference voltage $V_{REF}$. The supply voltage $V_{DD}$ is provided across a pair of transistors connected in series with a pair of capacitors and used to provide an input voltage $V_{IN}$, which is compared to the reference voltage $V_{REF}$ via a comparator 610. In steady-state, $V_{IN}$ is equal to $V_{REF}$. When the light generated by the photovoltaic diodes is modulated, then $V_{IN}$ is modulated and the output of the comparator 610 transitions between HIGH and LOW states. A stream chip ID signal is used to disable the optical receiver when a chip ID is sent out from the mote 500 to, for example, the repeater 122 of FIGS. 1-2. This may occur after clock recovery performed by the clock generation circuit 506.

Figure 7:
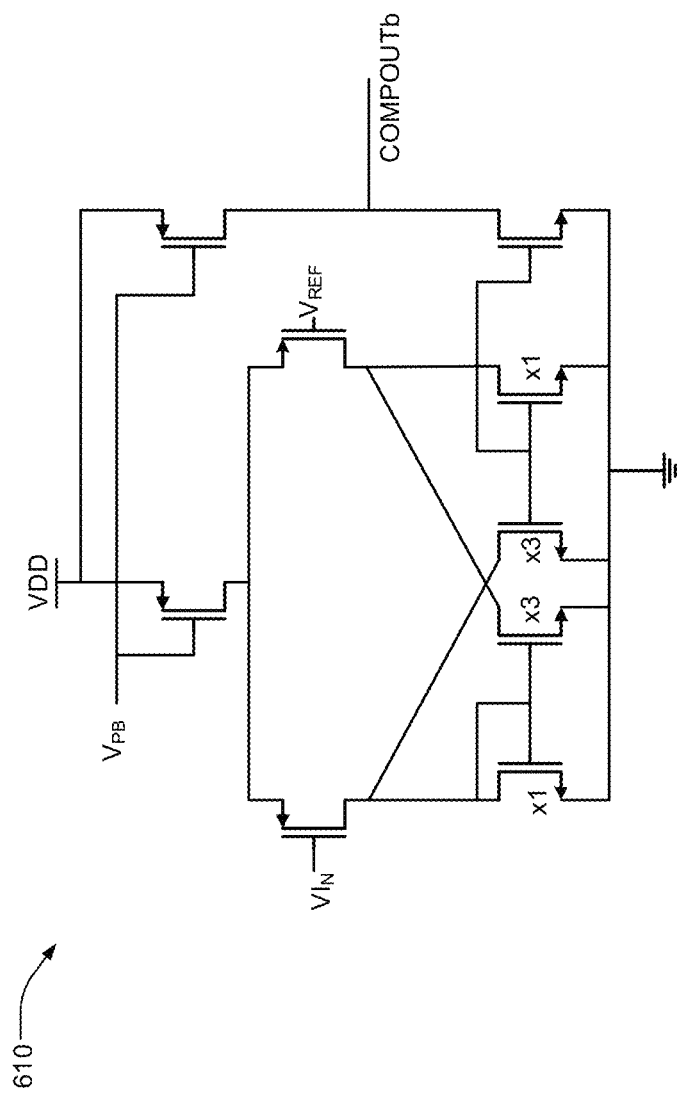
FIG. 7 is a schematic view of a comparator of the optical receiver of FIG. 6 in accordance with an embodiment of the present disclosure.

An example of the comparator 610 of the optical receiver 502 is shown in FIG. 7. The comparator 610 is a hysteresis comparator and is configured not to toggle when glitches occur in receive light. The comparator 610 includes differential transistors that receive $V_{IN}$ and $V_{REF}$. The signal COMPOUTb is generated based on the comparison of $V_{IN}$ and $V_{REF}$ and provided to a NOR gate of the optical receiver 502.

The reset number generator 504 generates a reset signal RSTN, which is used to reset, for example, flip-flops of the clock generation circuit 506 and the data recovery circuit 508. At boot-up, the PV signal transitions from 0-$V_{DD}$, which is input to the reset number generator 504. The RSTN signal transitions from '0' to '1'. The inverse of this is provided as reset signal RST.

The clock generation circuit 506 includes a default clock circuit 620, a clock recovery circuit 622, and an edge comparator 624. The default clock circuit 620 includes inverters, NAND gates and delay stages (or cells) and provides a default clock signal CLKDEF that is used prior to locking a recovered clock signal CLKREC of the clock recovery circuit 622 to, for example, a target clock frequency of the clock 228 of the repeater 122 of FIG. 2. In an embodiment, during clock recovery, each of the motes of the corresponding recording system are locked to the target clock frequency. An input of the clock recovery circuit 622 is based on the output of the optical receiver COM POUT, based on which signals IN and INb are generated and provided to flip-flops (FFs) as shown. A lock signal LOCK is generated when the clock recovery circuit 622 is locked onto the target frequency. The signal LOCKb is the inverse of LOCK. The signal LOCK is used to control glitch-free multiplexers 640 that select between the default clock signal CLKDEF and the clock recovery signal CLKREC. The multiplexers 640 provide clock signals CLK1-3, which are provided to the data recovery circuit 508, the non-overlap module 510 and the chip ID module 522. The clock signals CLK1-3 are locked to the target clock frequency and are out-of-phase from each other. As an example, the signals CLK1-3 may be 120° out-of-phase from each other. The signals S and S" are frequency signals.

Figure 8:
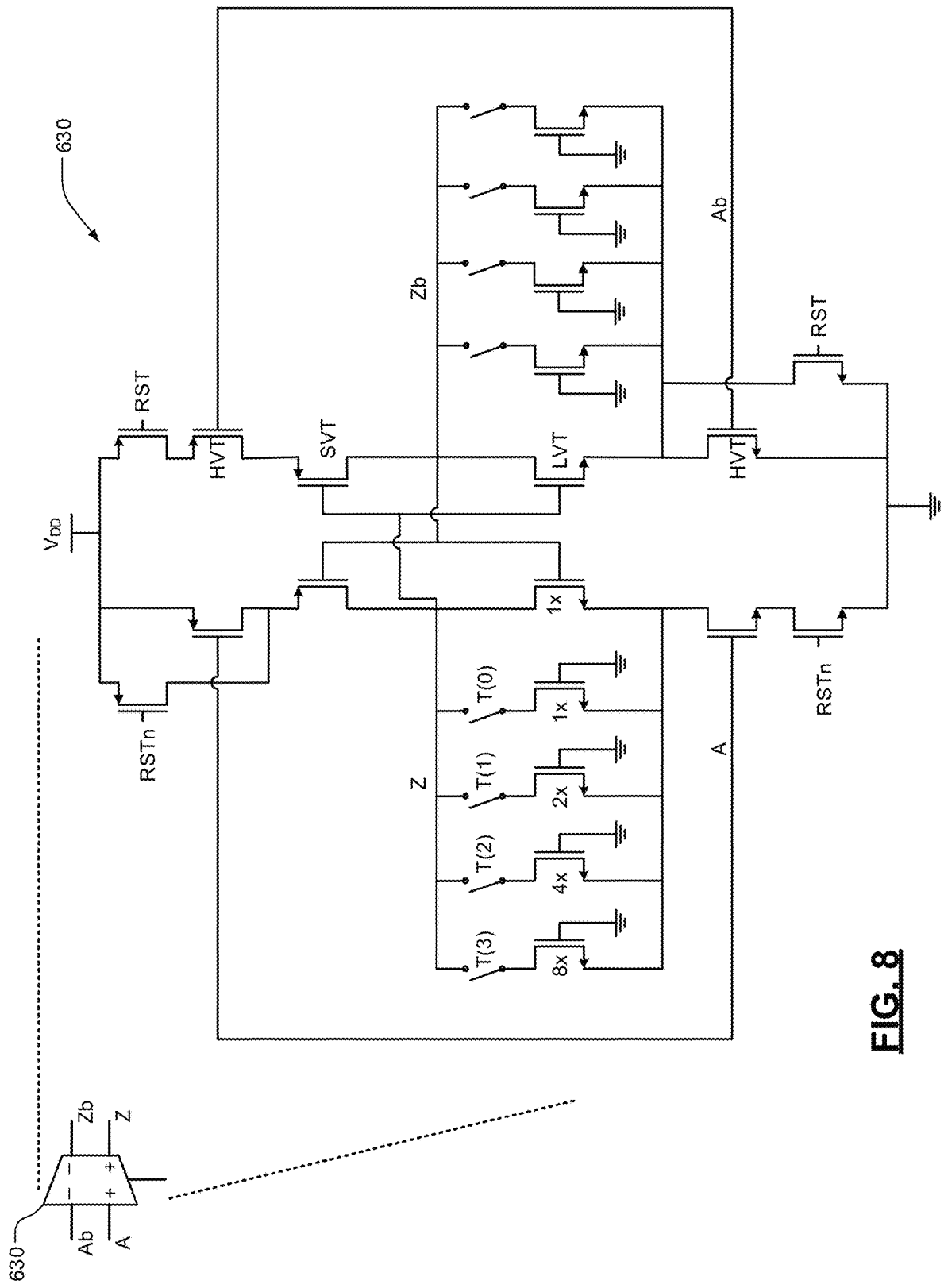
FIG. 8 is a schematic view of a digitally controlled delay stage of the clock recovery circuit of FIG. 6 in accordance with an embodiment of the present disclosure.

The clock recovery circuit 622 includes inverters, NAND gates, and a digitally-controlled oscillator (DCO) that includes multiple digitally-controlled delay stages (or cells) 630 that are connected in series. An example of one of the delay cells 630 is shown in FIG. 8. The delay cells are configured to set the frequency of the clock recovery circuit 622. Each of the delay cells includes transistors and corresponding switches that are connected in parallel and control a level of leakage current. The more of the switches that are closed, the more leakage current and the higher the frequency that is set. The output of the delay cell switches more frequently with higher leakage current. The input of the delay cell is provided as signals A and Ab and the output of the delay cell is provided as signals Z, Zb. The states of the switches are controlled by 4 bit switch oscillation signals T(0)-T(3), which are provided by the edge comparator 624. Reset signal RSTN is generated by the reset number generator 504. The reset signal RST is an inverse of the reset signal RSTN. LVT, HVT and SVT are low voltage threshold, high voltage threshold and standard voltage threshold signals.

The edge comparator 624 of FIG. 6 includes a flip-flop, a saturation detector and a 4 bit Up/Down counter and compares two edges; the first one is from external light modulation and the second one is from the clock recovery circuit. The edge comparator 624 then reduces frequency of the DCO until a target frequency is met by generating the switch oscillation signals T[3:0].

Figure 9:
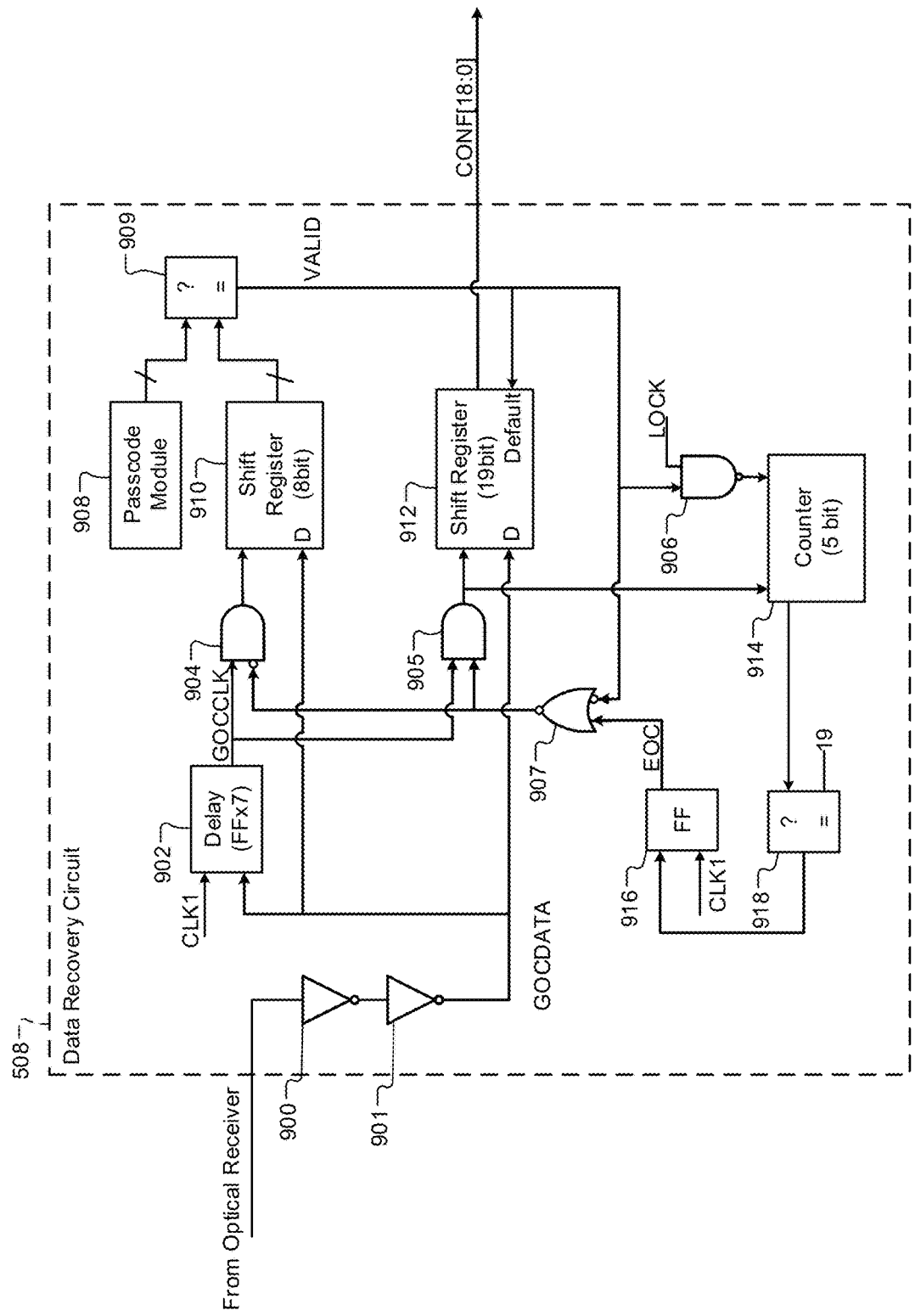
FIG. 9 is a schematic view of a data recovery circuit of the mote of FIG. 5 in accordance with an embodiment of the present disclosure.

An example of the data recovery circuit 508 is shown in FIG. 9 and includes inverters 900, 901, a delay module 902, AND gates 904, 905, 906, a NOR gate 907, a passcode module 908, a first comparator 909, an 8 bit shift register 910, a 19 bit shift register 912, a counter 914, a flip-flop 916, and a second comparator 918. The data recovery circuit 508 recovers data received via the optical receiver 502 and provide the data as signal CONF[18:0], which is sent to the integrator 518 of FIG. 5.

During operation of the data recovery circuit 508, when a received modulated signal (received 8 bits) in the 8 bit shift register 910 matches an 8 bit passcode stored in and/or generated by the passcode module 908, as determined by the first comparator 909, the 19 bit shift register 910 is enabled. 19 bits of received data is then sequentially shifted into the 19 bit shift register 912. The signal VALID is HIGH when there is an 8 bit match enabling the 19 bit shift register. After receiving the 19 bits of data, the signal VALID is reset to a LOW state. The 19 bits of data are used to configure sub-blocks, devices, and/or modules of the mote 500 including setting parameters of amplifiers, reference generators, LED driver, integrator, etc. This may include setting voltages, current levels, bandwidths, gains, thresholds, etc.

Referring back to FIG. 5, the non-overlap module 510 generates phase signals φ1 and φ2 based on the second clock signal CLK2. The phase signals φ1 and φ2 are 180° out-of-phase of each other and do not overlap. The phase signals φ1 and φ2 are used for switching capacitors of reference generators 512, 514. The phase signals φ1 and φ2 allow a first set of capacitors to be switched ON while another set of capacitors is switched OFF and vice versa, such that there are no overlapping periods when both sets of capacitors are ON and/or both sets of capacitors are OFF. The phase signals φ1 and φ2 are also provided to the 3-stage bandpass differential amplifier 516.

Figure 10:
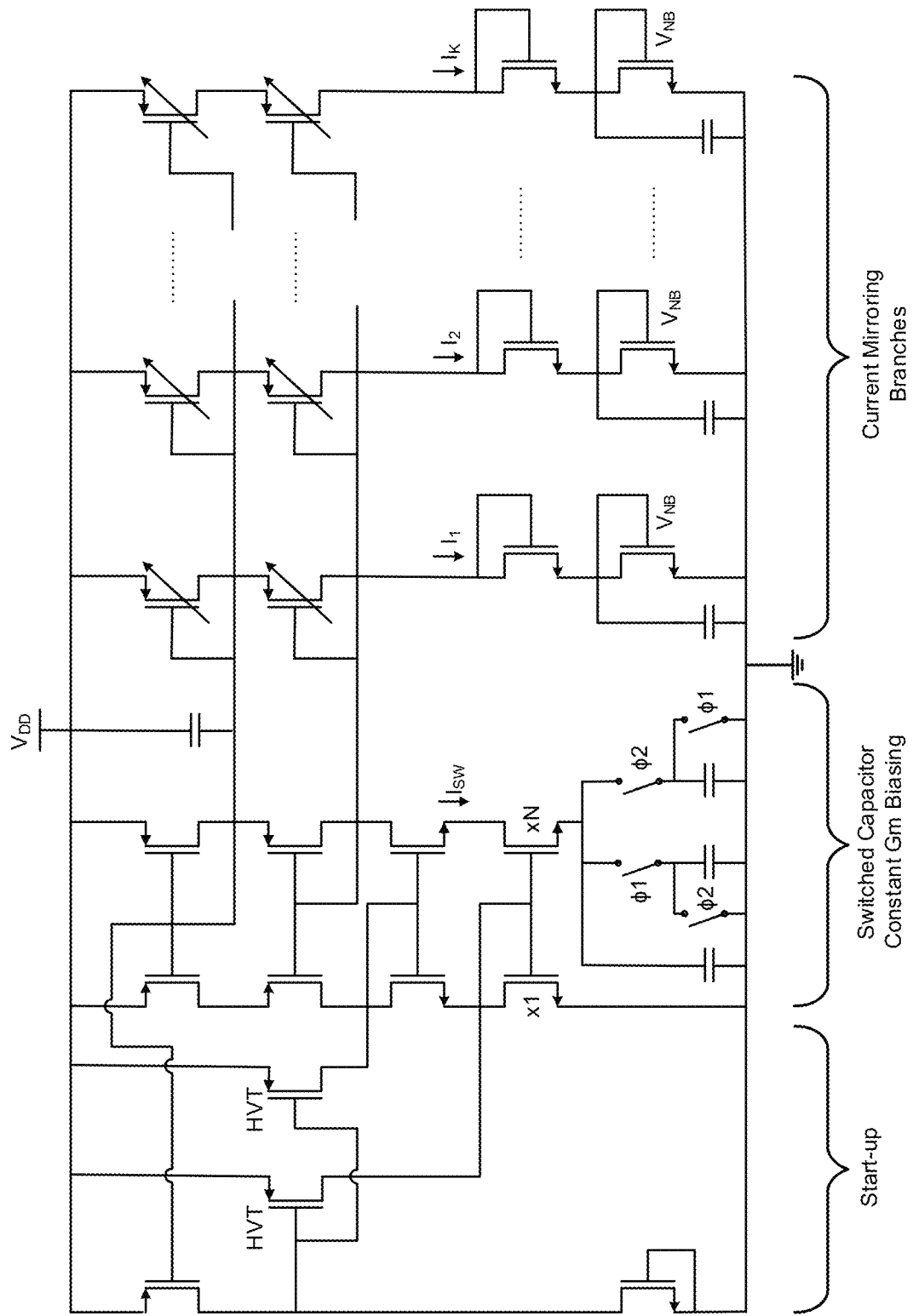
FIG. 10 is schematic view of a switched capacitor based current reference in accordance with an embodiment of the present disclosure.

An example of the current generator 512 is shown in FIG. 10. The current generator 512 is a switched capacitor based current generator and includes 3-stages, a start-up stage, a switched capacitor constant gain (Gm) biasing stage, and a third stage including current mirroring branches. The current mirroring branches provide current signals $I_1, I_2, \ldots I_K$. The current signals $I_1, I_2, \ldots I_K$ are based on frequency, which accurately affects resistance and as a result accurately affects the current levels of the current signals $I_1, I_2, \ldots I_K$. The voltage $V_{NB}$ at which the final transistors of the current mirroring branches are gated is provided to the 3-stage bandpass differential amplifier 516 of FIG. 5.

FIG. 11 shows an example signal diagram 1100 during clock and data recovery for signals $f_{CLK\_REC}$ and $V_{DD}$, GOCDATA, GOCCLK, UP, LOCK, VALID, and EOC, as shown in FIGS. 6 and 9. The signal diagram 1100 shows examples of these signals during which 8 bits are received and compared subsequent to accomplishing clock recovery. The signals also show an example of when 19 bits are received during data recovery and subsequent to matching the 8 bit passcode.

Figure 13:
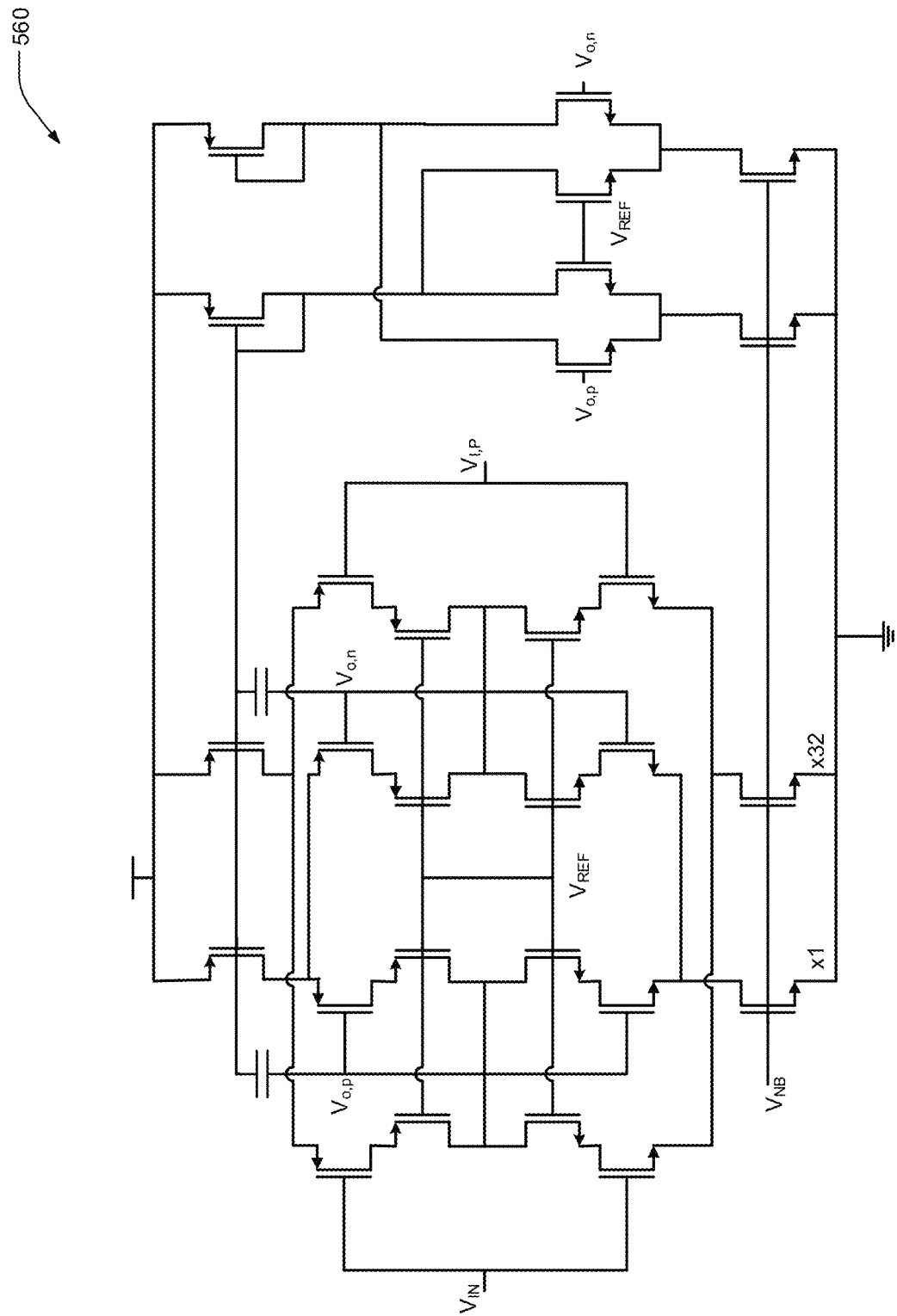
FIG. 13 is a schematic view of an example of an operational amplifier of the amplifier of FIG. 12 in accordance with an embodiment of the present disclosure.

Referring to FIGS. 5 and 12, which shows an example of the 3-stage bandpass differential amplifier 516. The bandpass differential amplifier 516 includes a low-noise amplifier (LNA) 550, a first voltage gain amplifier (VGA1) 552, a second voltage gain amplifier (VGA2) 554, and buffers 556. The LNA 550 receives the output of the electrode 540 (or $V_{IN}$) and is connected to the voltage reference terminal 542 at voltage potential $V_{REF}$. The voltage potential $V_{REF}$ may be obtained from a reference terminal at a bottom of the corresponding mote, such as the reference terminal 322 of FIG. 3, or from a reference terminal at a top of the corresponding mote, such as the reference terminal 404 of FIG. 4. The LNA 550 includes capacitors C1, C2, variable resistors R1, R2 and an amplifier 560. FIG. 13 shows an example of the amplifier 560 of FIG. 12. The amplifier 560 receives the voltages $V_{NB}$, $V_{REF}$, input voltages $V_{i,n}, V_{i,p}$ and provides output voltages $V_{o,n}, V_{o,p}$. The variable resistors R1, R2 receive ½ voltage $V_{DD}$ and variable resistance set signal FASTSET.

The VGA1 552 includes variable capacitors C3, C4, capacitors C5-C8, resistors R3, R4 and amplifier 562, which is shown in FIG. 12. The VGA2 554 includes variable capacitors C9, C10, C13, C14, capacitors C11, C12, switches 564-567, amplifier 568 and buffers 571. The switches 564-567 are controlled by the phase signals φ1 and φ2 and in combination with the capacitors C11 and C12 provide DC servo feedback loops. Resistances of the DC servo feedback loops are equal to the clock frequency divided by the respective capacitance (e.g., values of C11 or C12). The switches 564-567 are switched at the clock frequency. The output $V_{OUTN}$, $V_{OUTP}$ of VGA2 554 is provided to the rectifier-based analog integrator 518.

FIG. 14 shows an example of the rectifier-based analog integrator (or integration circuit) 518 of the mote 500 of FIG. 5. The rectifier-based analog integrator 518 receives the voltages $V_{REFH}$, $V_{REFN}$, $V_{REFP}$, and outputs integrated signal INTOUT. The rectifier-based analog integrator 518 includes an amplifier 1400, a rectifier 1402, and an integrator 1404. The rectifier 1402 converts an analog signal to a rectified signal, which is integrated by the integrator 1404 to provide the integrated signal INTOUT. The integrator 1404 integrates accumulated power in the charge domain. The integrated signal INTOUT is compared with the voltage threshold $V_{REFL}$ via the comparator 520. The output of the comparator is provided to inverters to provide signal LEDEN. The output of the integrator INTOUT is precharged to $V_{REFH}$.

When a signal is received (i.e. spiking band power is detected) at the electrode 540 of FIG. 5, then INTOUT drops. Integration occurs over the SBP 300-1000 Hz band, which is dominated by a single neuron. When the integrated power or INTOUT drops below the threshold $V_{REFL}$, then the LEDEN signal is triggered to pulse the LED 570 of FIG. 5. The pulsed signal sent out from the LED 570 is received at the corresponding photodiodes of the NIR transceiver of the repeater 122 of FIG. 2. INTOUT is then reset to $V_{REFH}$. If there is no signal on $V_{IN}$, then INTOUT remains at $V_{REFH}$. If there is a signal on $V_{IN}$, then INTOUT drops below $V_{REFL}$ and LEDEN is pulsed. If the time interval between LED pulses is long, then there are a small number of spikes on $V_{IN}$.

A unique chip ID packet is sent out from the mote 500 of FIG. 5 to the repeater 122 of FIG. 2 to indicate to the repeater 122, which one of the motes 124 is providing the corresponding signal. This may be done prior to pulsing the LED 570 based on $V_{IN}$. Symbol interval modulation is implemented when transmitting signals via the LED 570 using the LED driver 526. Time intervals between transmitted symbols provides information such as voltages of the input $V_{IN}$. The mote 500 is operated and the LED 570 is triggered to minimize heat generation, thereby preventing damage to tissue of patient. Power exposure is limited, such that change in surrounding tissue temperatures does not change more than 1° C.

Figure 15:
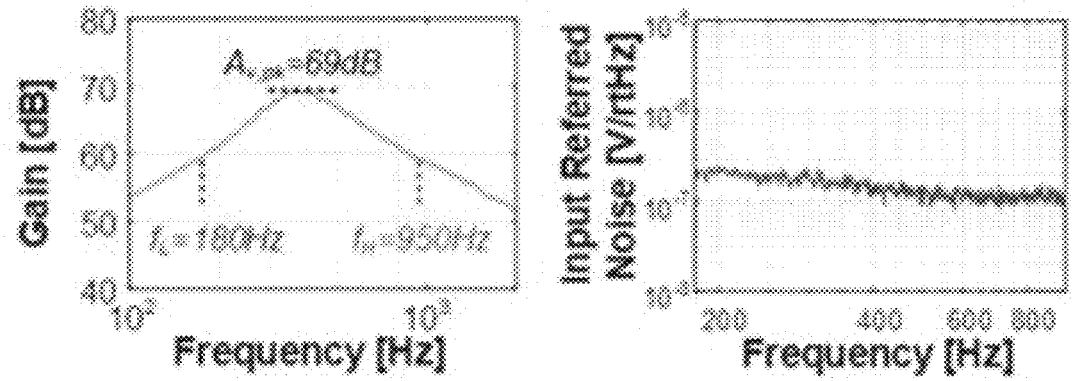
FIG. 15 is an example diagram of gain and input referred noise versus frequency plots of the 3-stage bandpass differential amplifier of FIG. 12 in accordance with an embodiment of the present disclosure.

FIG. 15 shows gain and input referred noise vs frequency plots of the 3-stage bandpass differential amplifier 516. FIG. 16 shows example in vivo transient measurement results on a rat cortex monitoring a rat motor cortex neural signal. The results include $V_{IN}$, $V_{OUT}$, INTOUT, and data over time. As shown by the INTOUT signal plot, the INTOUT signal steps down for each "firing" or pulsing of the LED 570. At each spike on $V_{IN}$, voltage discharges and drops voltage of the signal INTOUT.

FIG. 17 shows an example Manchester encoded chip identifier (ID), which may be generated by the chip ID reset number generator 524 and transmitted by the chip ID module 522 via the LED driver 526. The time T is inversely proportional to the SBP detected.

FIG. 18 show measured linearity of a LED firing rate across SBP for synthesized SBP spikes generated by a simulator and provided to $V_{IN}$ of the mote 500. The spiking rate was swept between 0-100 Hz. Action potential spikes with 240 µV peak-to-peak voltage and 1 ms pulse widths. The SBP values were calculated using computer programming software (e.g., MATLAB®) on a computer, such as the monitoring station 100 of FIG. 1.

Figure 19A:
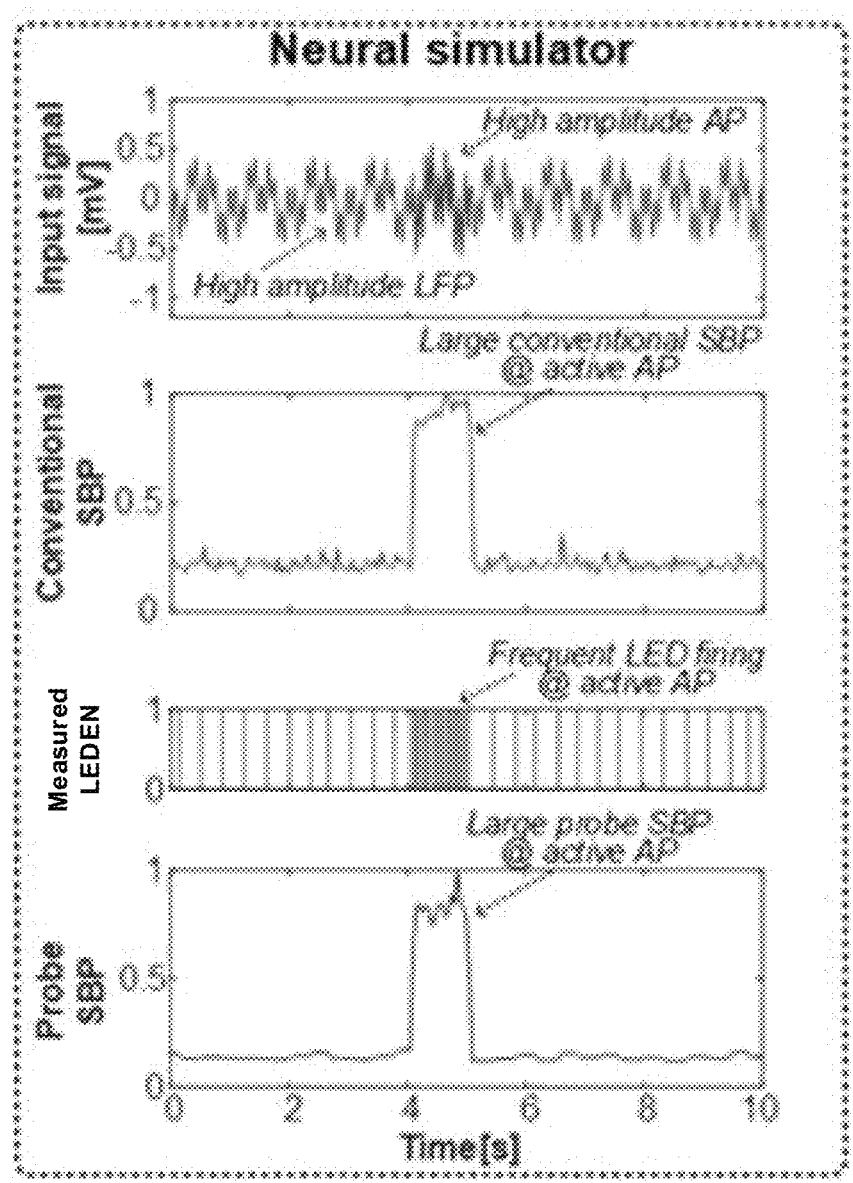
FIG. 19A is an example diagram of measured linearity of light emitting diode (LED) firing rate across SBP in accordance with an embodiment of the present disclosure.
Figure 19B:
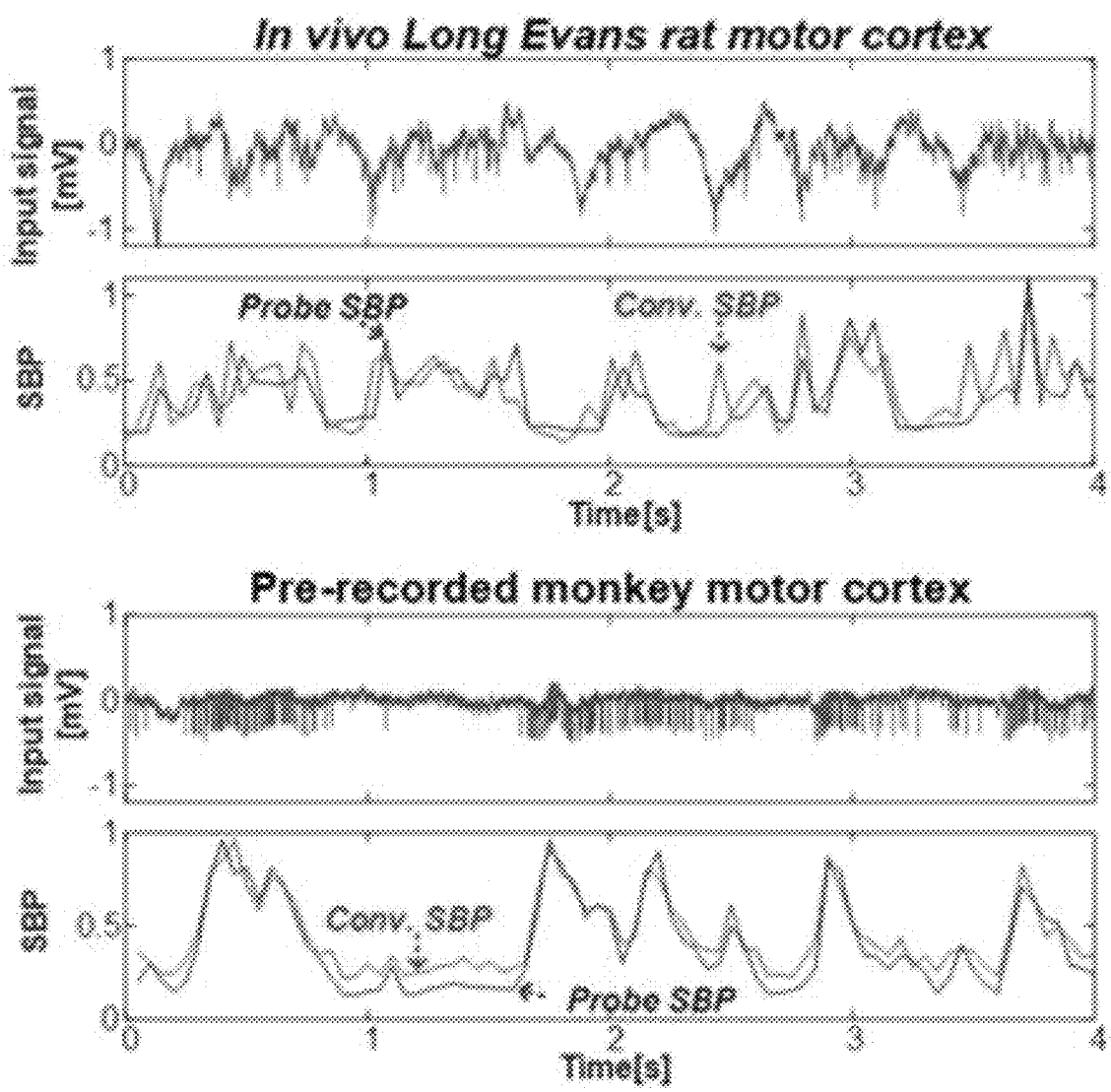
FIG. 19B is an example diagram of measured transient waveforms from three types of input neural signals in accordance with an embodiment of the present disclosure.

FIGS. 19A and 19B show measured transient waveforms from three types of input neural signals. FIG. 19A shows neural simulation plots for which simulated neuron signals were generated and provided as an input to the mote 500. High amplitude action potential (AP) portions of the input signal were monitored. As shown the probe (or more) SBP signal closely matches a conventional SBP signal, which are high when there is high amplitude APs. The measured LEDEN signal illustrates when a chip ID packet is transmitted. Time intervals between edges of the CHIP ID packet are determined to generate the probe SBP signal shown. This may be implemented by, for example, the external device 120 and/or the monitoring station 100 of FIG. 1. FIG. 19B shows input and SBP signals for In vivo Long Evans rat motor cortex and input and SBP signals for pre-recorded monkey motor cortex illustrating differences between a probe (or mote) SBP results and conventional SBP results. As shown the probe SBP results closely follow the conventional SBP results.

FIG. 20 shows a finger position/velocity decoding result for a probe (or mote) as disclosed herein and conventional recording system. The differences in position and velocity values for the probe versus the conventional recording system are negligible.

FIG. 21 shows a comparison table of parameters and features of different recording systems including parameters and features for one of the wireless neural recording systems disclosed herein. The second full column of the table is associated with the wireless neural recording systems disclosed herein using optical transmission techniques and SIM, as described herein. Values for three other recording systems, which implement RF with binary phase-shift-keying (BPSK)-modulated RF backscatter, ultrasonic with amplitude modulation (AM) backscatter, and optical with pulse position modulation (PPM) techniques are also shown and refer respectively to: J. Lee, et. al., "an implantable Wireless Network of Distributed Microscale Sensors for Neural Applications," Int. *IEEE/EMBS NER*, pp. 871-874, 2019; M. M. Ghanbari, et. al., "A 0.8 mm² Ultrasonic Implantable Wireless Neural Recording System with Linear AM Backscattering," *ISSCC* Dig. Tech. Papers, pp. 284-285, February 2019; and S. Lee, et. al., "A 330 µm×90 µm Opto-Electronically Integrated Wireless System-on-Chip for Recording of Neural Activities," *ISSCC* Dig. Tech. Papers, pp. 292-293, February 2018."

FIG. 22 shows an example chip layout of a mote 2200. In one embodiment, the chip is 170 µm×190 µm as shown. The mote 2200 is shown having multiple components (e.g., modules, amplifiers, an integrator, generators, oscillators, a receiver, etc., some of which are shown. The components provide various features identified as $V_{DD}$, $V_{SS}$, $V_{IN}$, $V_{LED}$, REF, etc. some of which are shown.

Figure 23:
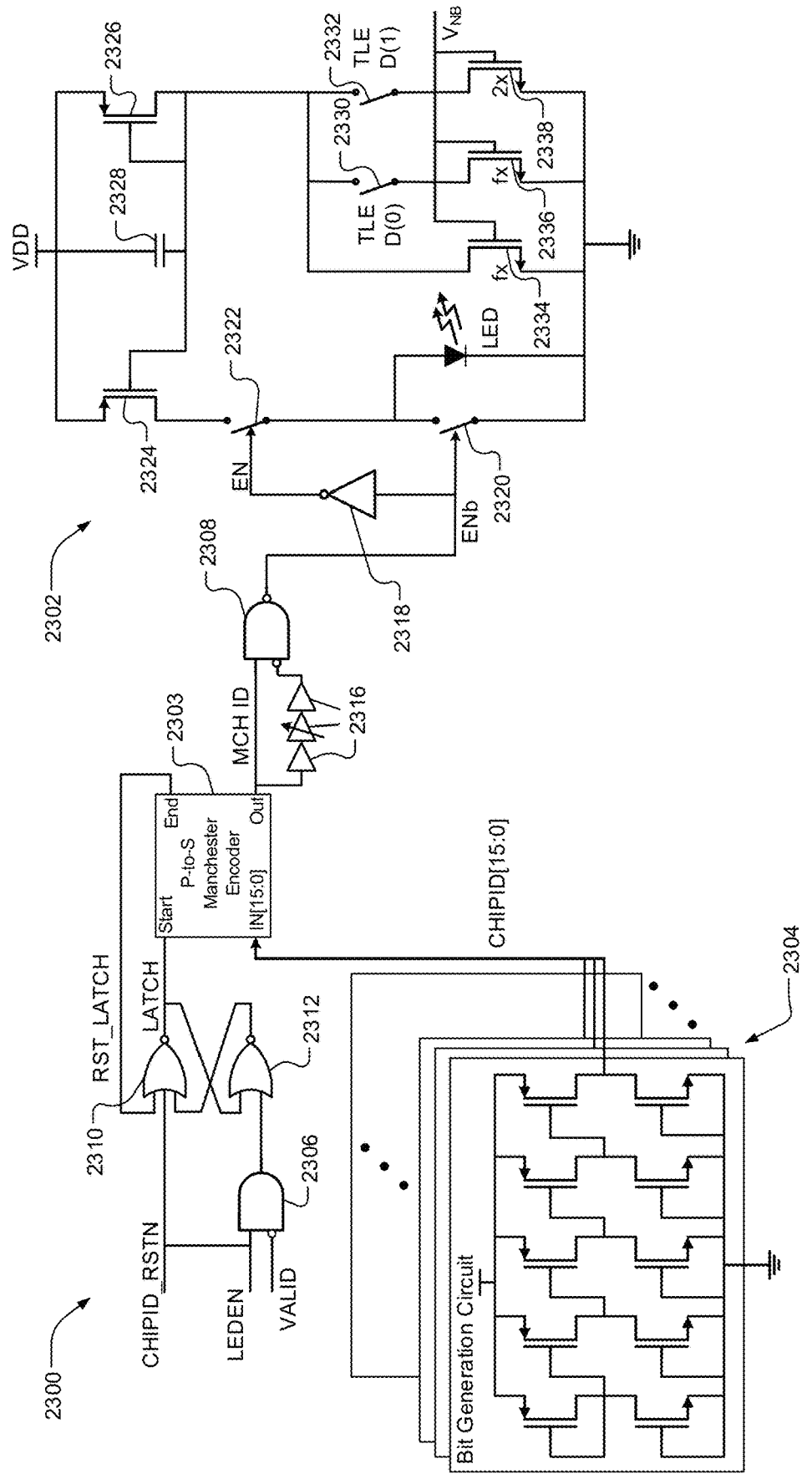
FIG. 23 is a schematic view of an example of a chip ID circuit and a LED driver of the mote of FIG. 5 in accordance with an embodiment of the present disclosure.

FIG. 23 shows a chip ID circuit 2300 and LED driver 2302, which may be implemented in one of the motes disclosed herein. The chip ID circuit 2300 is an example of the chip ID module 522 of FIG. 5. The LED driver 2302 is an example of the LED driver 526 of FIG. 5. The chip ID circuit 2300 includes bit generation circuits 2304, an AND gate 2306, a NAND gate 2308, NOR gates 2310, 2312, a parallel-to-series Manchester encoder 2303, buffers 2316, and an inverter 2318. The bit generation circuits 2304 provide 16 bits as signal CHIPID[15:0] to an input of the encoder 2303. The AND gate 2306 receives the signals CHIPID_RSTN, LEDEN, VALID. The NOR gate 2310 receives the signal CHIP_RSTN and an output of an end terminal of the encoder 2303. The NOR gate 2312 receives an output of the AND gate 2306. Outputs of the NOR gates are provided to a start input of the encoder 2303. An output of the encoder 2303 is provided to the buffers 2316 and the NAND gate 2308. An output of the NAND gate 2308 is provided to the inverter 2318 and to a first switch 2320 of the LED driver 2302.

The LED driver 2302 includes switches 2320, 2322, transistors 2324, 2326, a capacitor 2328, switches 2330, 2332 and transistors 2334, 2336, 2338. The transistors 2324, 2326 and capacitor 2328 are connected to receive $V_{DD}$. The switches 2330, 2332 are connected in series with the transistors 2336, 2338. Gates of the transistors 2334, 2336, 2338 receive $V_{NB}$. An output LED (e.g., the LED 570 of FIG. 5) is connected across the switch 2320. The switches 2330, 2332 are controlled by signals TLED(0) and TLED(1). The LED driver 2302 operates as a digital to analog converter.

Figure 24:
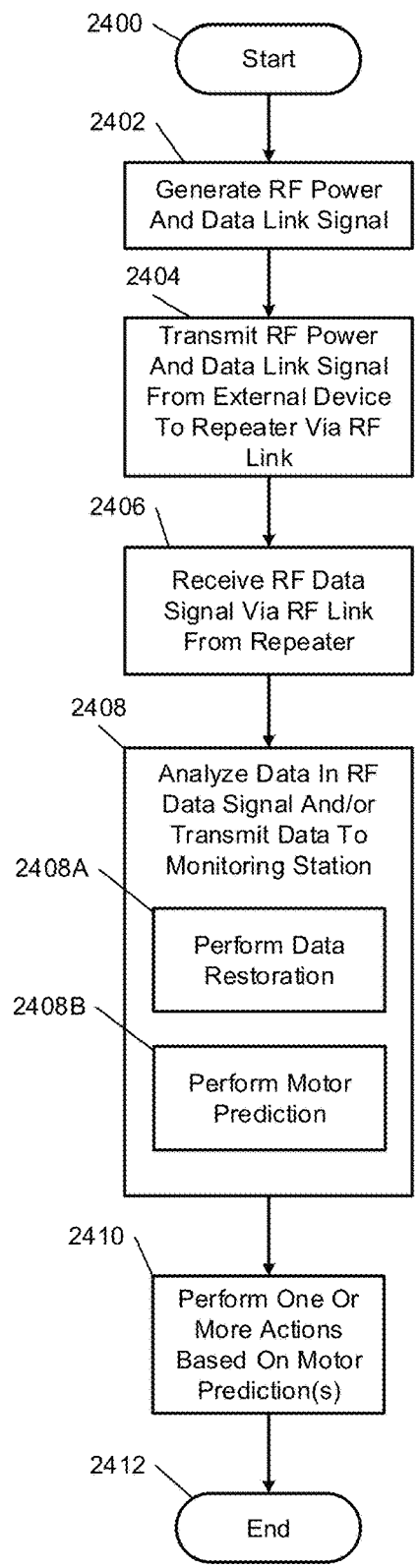
FIG. 24 illustrates a method of operating an external device in accordance with the present disclosure.
Figure 25:
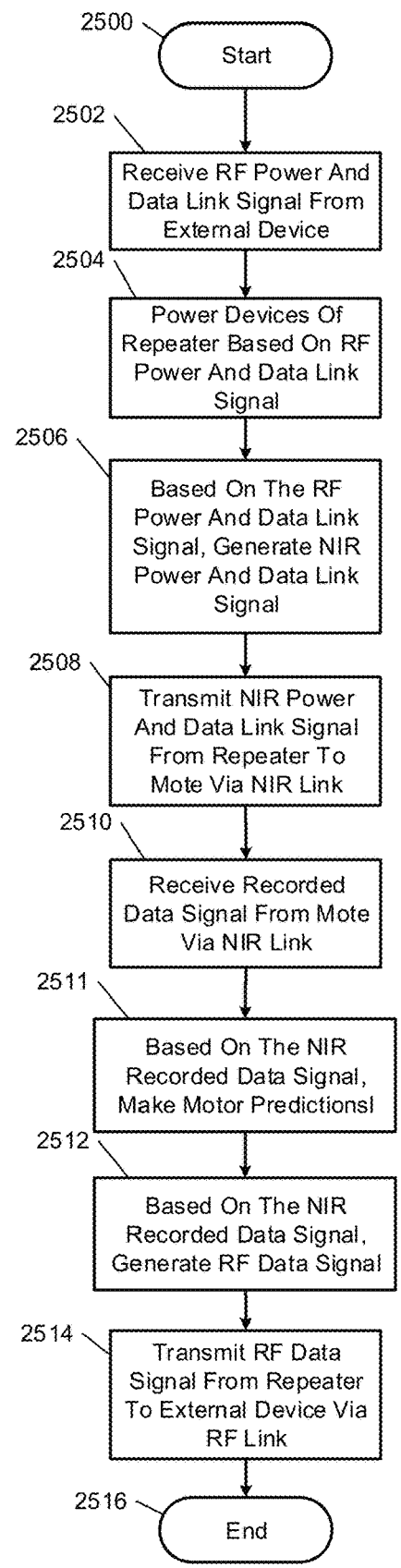
FIG. 25 illustrates a method of operating a repeater in accordance with the present disclosure.
Figure 26:
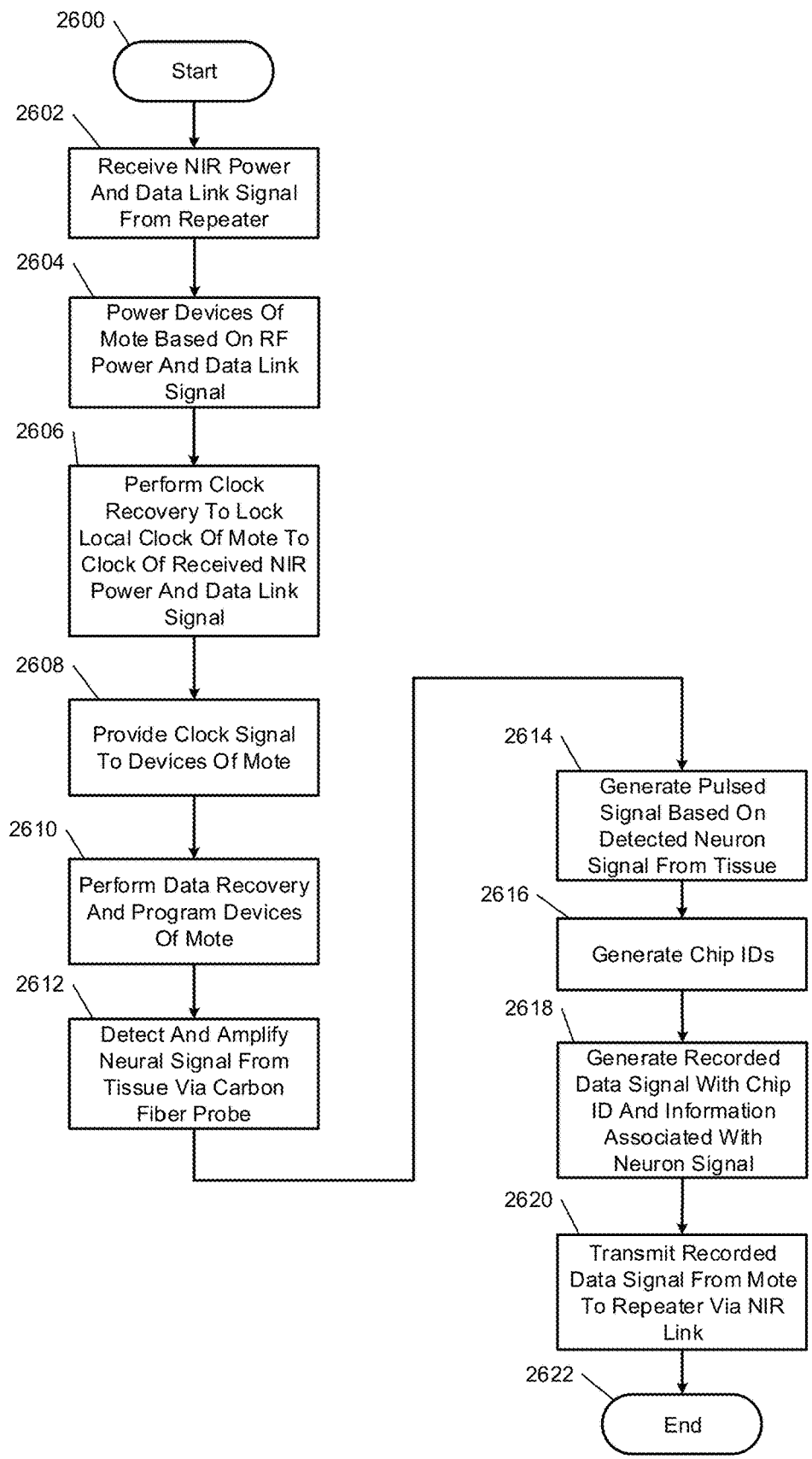
FIG. 26 illustrates a method of operating a mote in accordance with the present disclosure.

The systems disclosed herein may be operated using numerous methods, example methods are illustrated in FIGS. 24-26. In FIG. 24, a method of operating the external device 120 is shown. Although the following methods are shown as separate methods, the methods and/or operations may be combined, implemented during a same period of time, and/or performed as a single method. Although the following operations are primarily described with respect to the implementations of FIGS. 1-5, the operations may be easily modified to apply to other implementations of the present disclosure. The operations may be iteratively performed.

The method may begin at 2400. At 2402, the control module 200 of the external device 120 generates a RF power and data link signal via the RF transceiver 202. At 2404, the RF transceiver 202 transmits (or downlinks) the RF power and data link signal to the RF transceiver 224 of the repeater 122. The RF power and data link signal is transmitted over a preselected radio frequency and includes programming information for programming the motes 124.

At 2406, the control module 200 receives one or more RF data signals from the RF transceiver 224 of the repeater 122 via the RF transceiver 202. The one or more RF data signals may be associated with one or more motes and are generated in response to the previous power and programming information supplied via the RF power and data link signal. Each RF data signal may be associated with one or more motes.

At 2408A, the control module 200 performs data restoration to recovery the data included in the RF data signals. The external device is able to identify which data belongs to which mote. The RF data signals may include chip identifiers of the motes or another indication provided by the repeater 122 indicating which mote provided which data. In one embodiment, the RF data signals include motor predictions made by the repeater 122. The RF data signals may include other information, such as neuron signal voltages, SBP values and/or other data collected and/or determined by the motes 124 and/or the repeater 122.

At 2408B, the control module 200 may perform motor predictions based on the recovered data. This may be based on the information transferred from the motes 124. At 2410, the control module 200 may perform one or more actions based on the motor predictions. As a couple of examples, the actions may include: signaling the motor predictions to the monitoring station 100 of FIG. 1 for further analysis; and/or controlling operation of one or more motors and/or actuators used to control movement of one or more limbs and/or mechanical devices. The method may end at 2412.

FIG. 25 shows a method of operating the repeater 122 of FIG. 5. The method may begin at 2500. At 2502, the RF transceiver 224 of the repeater 122 receives the RF power and data link signal from the RF transceiver 202 of the external device 120.

At 2504, the control module 220 charges the power source 223 and/or supplies power to modules, transceivers and other devices of the repeater 122 based on power received from the RF power and data link signal.

At 2506, the control module 220, based on the RF power and data link signal, generates via the NIR transceivers 226 NIR power and data link signals. At 2508, the NIR transceivers 226 transmit (or downlinks) the NIR power and data link signals via the LEDs 230 from the repeater 122 to the photovoltaic diodes 246 of the motes 124.

At 2510, the control module 220 receives recorded data signals from the motes 124 via the NIR link. At 2511, the control module 220 may make motor predictions based on the recorded data signals, neuron signal voltages, frequency of the LED 570 of FIG. 5, SBP values and/or historical data stored in the memory 222. The control module 220 may determine SBP values based on the received NIR recorded data signals. As an example, the firing rate or frequency of the LED 570 of FIG. 5 is directly proportional to the SBP.

At 2512, the control module 220, based on the recorded data signals, generates RF data signals. In one embodiment, the recorded data signals are decoded prior to being converted to RF data signals based on pre-stored unique chip IDs of the motes 124 stored in the memory 222 of the repeater 122. The decoding may include in the following order determining time intervals to SBP periods, performing a position Kalman filter training/prediction process, and/or predicting finger position and/or velocity. The information in the received NIR recorded data signals may be included in the RF data signals. In one embodiment, this includes the chip identifiers. In another embodiment, this includes another indication identifying which mote the corresponding data was received from. The RF data signals may include the motor predictions, SBP values, neuron signal voltages, and/or other data and/or information collected from motes 124. At 2514, the control module transits the RF data signals from the repeater 122 to the external (or remote) device 120 via the RF transceiver 224. The method may end at 2516.

FIG. 26 shows a method of operating one of the motes 124 of FIG. 5. The method may begin at 2600. At 2602, the NIR transceivers 244 of the motes 124 receive the NIR power and data link signals via the photovoltaic diodes 246.

At 2604, the control module 240 of the motes 124 supplies power in the form of the signal $V_{DD}$ to modules, transceivers and other devices of the motes 124 as described above based on power received from the NIR power and data link signals.

At 2606, the clock generation circuits of the motes 124 perform clock recovery to lock a local clock of each of the motes 124 to the clock of the repeater 122. This is based on the NIR power and data link signal as described above. At 2608, the clock generation circuits provide recovered clock signals to devices of the motes 124.

At 2610, the data recovery circuits of the motes 124 perform data recovery on the NIR power and data link signals, which may be modulated to provide values for setting parameters of the devices of the motes 124 as described above.

At 2612, the 3-stage bandpass differential amplifiers of motes 124 detect and amplify neural signals received via carbon fiber electrodes, which are disposed in tissue of a patient. At 2614, the rectifier-based integrators of the motes 124 generate pulsed signals based on the neuron signals, as described above.

At 2616, the chip ID reset number generators of the motes 124 generate respective unique chip IDs of the motes 124. At 2618, the chip ID modules of the motes 124 generate recorded data signals using symbol interval modulation. Each of the recorded data signal includes a corresponding chip ID and information associated with one of the neuron signals. In one embodiment, the recorded data signals are encoded with the unique chip IDs using an ultra-low power physically unloadable function (PUF). This allows the signals from the motes 124 when received at the repeater to be distinguishable. At 2620, the LED drivers of the motes 124 transmit via the LEDs 248 of the motes the recorded data signals to the repeater 122 via the NIR transceivers 244. The frequencies of the LEDs 248 may be directly proportional to the SBP of the generated neuron signals. The method may end at 2622.

The above-described operations of FIGS. 24-26 are meant to be illustrative examples. The operations may be performed sequentially, synchronously, simultaneously, continuously, during overlapping time periods or in a different order depending upon the application. Also, any of the operations may not be performed or skipped depending on the implementation and/or sequence of events.

The above provided examples include a two-stage approach for long-term recording and transmitting of neural signals at a level of single neurons. An external device is used to communicate with a repeater implanted in a skull using RF. The repeater communicates with miniaturized motes floating on top of tissue using NIR light. Photovoltaic cells of the motes transfer light energy provided from the repeater to electrical energy used by circuits of the motes. Carbon fiber electrodes are used to penetrate into tissue to detect electrical potentials in the tissue. The motes acquire neural signals using ultra-low power analog front ends of the motes. The recorded signals are encoded with unique chip IDs to be distinguishable by the repeater. The motes send the recorded signals with the encoded chip IDs using NIR LEDs to the repeater, where the signals are received by single-photon avalanche diodes as optical receivers. The repeater decodes the received signals from the motes, converts the received signals to RF signals and sends the RF signals to the external device.

Figure 27:
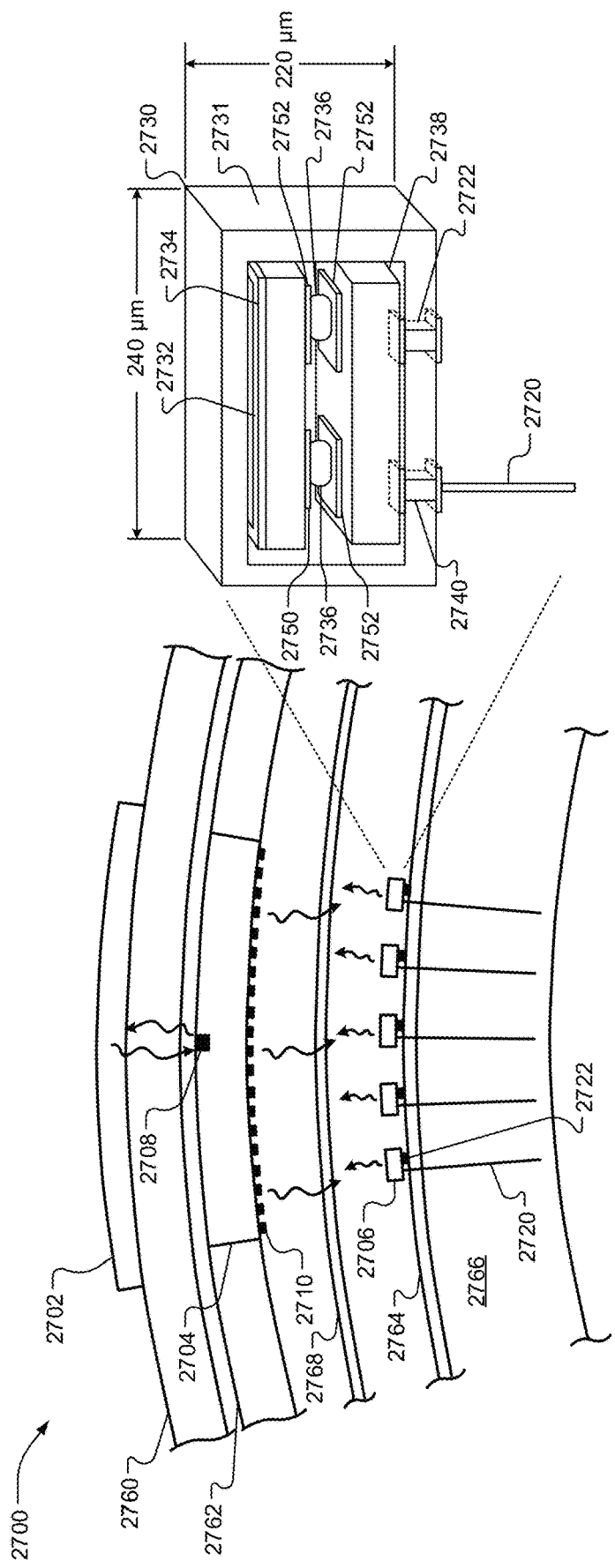
FIG. 27 is a cross-sectional view of the wireless neural recording system including a cross-sectional view of an example of a mote including an RF transmitter in accordance with an embodiment of the present disclosure.

FIG. 27 shows another example wireless neural recording system 2700 that includes an external device 2702, a repeater 2704 and motes 2706. The wireless neural recording system 2700 may replace and/or operate similar to the wireless neural recording system 300 of FIG. 3, except instead of using NIR LEDs at the motes for data uplink, RF antennas are used. The repeater 2704 includes an RF transceiver 2708 and NIR transmitters 2710. The motes 2706 include electrodes (e.g., carbon fibers) 2720 and reference terminals 2722. A cross-sectional perspective view of one of the motes 2730 is shown. The mote 2730, as with the other ones of the motes 2706, may include a housing 2731, a RF antenna 2732, a photovoltaic (PV) cell 2734, bonding balls 2736, a chip (e.g., a CMOS chip) 2738, a voltage input terminal 2740 connected to one of the electrodes 2720, and one of the reference terminal 2722 (one of the reference terminals 322). The bonding balls 2736 are connected to terminals 2750, 2752 of the PV cell 2734 and the chip 2738. The external device 2702 is disposed on a scalp 2760. The repeater 2704 is disposed in a skull 2762.

The motes 2706 are disposed on a pia mater 2764 above a cerebral cortex 2766 and below dura mater 2768. The reference terminals 2722 are in contact with the pia mater 2764 and provide a reference voltage potential. In an embodiment, the motes 2706 are floating on top of brain tissue. The motes 2706 are μm-scaled and each include a respective carbon fiber and circuit. Photovoltaic diodes of the motes 2706 collect light energy provided by the repeater 2704 and convert the light energy to electrical energy to power devices of the motes 2706. The carbon fibers penetrate tissue to detect electrical potentials of the tissue. The motes 2706 acquire neural signals in the tissue using ultra-low power analog front ends, as further describe below. As an example, each of the motes 2706 may be 240 μm wide with a height of 220 μm, as shown. In one embodiment, a volume of the housing is less than 250 μm$^3$.

The RF antenna 2732 may be implemented on the PV cell 2734 as shown or on the chip 2738. The PV cell 2734 or the chip 2738 may include a RF transmitter that transmits RF signals via the RF antenna 2732 to the repeater 2704. The RF antenna 2732 may include a metal coil antenna and is used for RF based inductive data uplink to the repeater 2704. An RF transceiver and/or metal antenna coils of the repeater may be used to receive the data transmitted from the RF antenna 2732 to the repeater 2704 instead of using one or more SPADs. This transmission may include the repeater 2704 using backscattering through mote antenna impedance modulation. The repeater 2704 records the RF signals received from the motes 2706. The repeater 2704 may encode the recorded signals using unique chip IDs generated by the on-chip ultra-low power physically unloadable function (PUF) as described above. This allows the recorded signals to be distinguishable by providing an indication as to which one of the motes each set of data belongs.

The motes (e.g., motes 124, 306, 2706) may be installed on mater, such as pia mater or arachnoid mater using various techniques. A few examples are described with respect to FIGS. 28-31. FIG. 28 shows an insertion diagram illustrating insertion of neural recording motes 2800 using a dissolvable substance and/or mold 2802. Neural recording motes may refer to any motes disclosed herein. As an example, the dissolvable substance and/or mold 2802 may include polyethylene glycol. Three stages 2810, 2812, 2814 are shown. In the first stage 2810, the motes 2800 are disposed in the dissolvable substance and/or mold 2802. In the second stage 2812, the dissolvable substance and/or mold 2802 and the motes 2800 are placed on an insertion plane 2816, which may refer to generally an outer, top and/or tangential surface of mater (or tissue of a patient) on which the motes are to be placed. Although the insertion plane 2816 and other insertion planes referred to herein are shown as being planar, the corresponding motes may be inserted along a non-planar surface of the mater. The dissolvable substance and/or mold 2802 is dissolved by introduction of a solvent 2818. In the third stage, the dissolvable substance and/or mold 2802 has dissolved and the motes 2800 are attached to the mater. Although not shown in FIG. 28, the motes 2800 may include carbon fibers that extend through the insertion plane 2816 and into the mater.

FIG. 29 shows another insertion diagram illustrating insertion of neural recording motes 2900 using a multi-layer material stack (referred to as a "gel pak") 2902. The multi-layer material stack 2902 may refer to and/or include a film layer gel bonded to a substrate material layer and having an adhesive side for attaching the motes 2900. In the example shown, top surface 2904 has an adhesive, which is part of an adhesive layer. The motes 2900 are placed upside down on the adhesive layer 2904, as shown by a first stage 2910, such that the motes 2900 are inverted.

At a second stage 2912, the motes 2900 and the multi-layer material stack are flipped over and disposed over mater on which the motes 2900 are to be placed. The multi-layer material stack is curled, as shown at the second stage 2912 to place the motes one-at-a-time, or one row-at-a-time if an array of motes are being placed, on the mater (shown as insertion plane 2920). Using a rolling motion from one side of the insertion site to the other, fibers of the motes 2900 are inserted into the mater and the multi-layer material stack is peeled off of the motes 2900 (referred to as "inserted devices").

At a third state 2914, the multi-layer material stack 2902 is peeled away from the motes 2900. The coupling between the motes 2900 and the mater is stronger than the adherence of the motes 2900 to the multi-layer material stack 2902, which allows the multi-layer material stack 2902 to be removed from the motes 2900.

FIG. 30 shows a top view of a mold 3000 for multiple neural recording motes 3002, such as any of the motes referred to herein, and insertion thereof. In the example shown, an array of motes are disposed in the mold 3000, some of which are designated 3002. The mold may be formed of silicon and/or other suitable material and may be referred to as a "cupcake" mold. The mold 3000 includes an array of recessed pockets 3004 for respectively holding the motes. The recessed pockets 3004 are sized and shaped to be similar to and/or match outer dimensions of the motes. The recessed pockets 3004 are sized relative to the motes and the mold 3000 may be flexible and/or stretch to aid in holding the motes in place. The mold 3000 may be a mirroring silicone baking mold that includes recesses made to fit each mote and hold it until insertion. During an insertion process, the mold 3000 is inverted and then peeled off in a rolling motion while gently pulling the mold to release the motes, which are attached to mater. This is similar to the insertion process described above with respect to the embodiment of FIG. 29.

FIG. 31 shows an insertion diagram 3100 illustrating a vacuum pick and place method for insertion of neural recording motes 3102, such as any the motes referred to herein. The motes 3102 are placed in a mold, represented by grid 3106, that allows the motes 3102 to sit with corresponding fibers hanging down. As an example and described with respect to one of the motes 3102, a vacuum device 3104 applies vacuum pressure on a back (or bottom) side of the mote. The mote is then lifted from the mold (or container) without disturbing the corresponding carbon fiber and is moved and inserted on mater, represented by insertion plane 3108. The vacuum is released and the process is repeated to insert the next mote. Transitioning from insertion of one mote to insertion of a next mote is represented by the arrows 3110. This process could be automated and have several vacuum systems and devices running concurrently to fill in different regions, which may include inserting one or more arrays of motes.

In the example shown the vacuum device 3104 may be a tube through which air is drawn via a vacuum pump 3120, which is controlled by a control module 3122. The control module 3122 may be the control module 200 of the external device 120 of FIG. 2. The vacuum device 3104, may be connected to the vacuum pump 3120 via, for example, an air line (not shown). The vacuum pump 3120 draws air from the vacuum device (or tool) 3104, which creates a vacuum on a side (e.g., top side) of one or more motes in order to lift, move and place the one or more motes. The vacuum device 3104 may be moved via a robot (not shown). The robot may include the vacuum device 3104 and/or the vacuum pump and be controlled by the control module 3122.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A mote configured to be implanted within a patient, the mote comprising:
   an optical receiver configured to wirelessly receive a first power and data signal in form of near infrared light energy within the patient and convert the near infrared light energy to an electrical signal having a supply voltage;
   a control module configured to power devices of the mote by supplying the supply voltage to the devices;
   a clock generation circuit configured to lock onto a target clock frequency based on the first power and data signal and generate a plurality of clock signals;
   a data recovery circuit configured to set parameters of one or more of the devices based on the first power and data signal and a first one of the plurality of clock signals;
   a first amplifier configured to amplify a neuron signal detected via an electrode inserted in tissue of the patient;
   a chip identifier module configured to, based on a second one of the plurality of clock signals, generate a recorded data signal, wherein the recorded data signal is generated based on a chip identifier of the mote and the neuron signal; and
   a driver configured to transmit the recorded data signal from the mote via a first light emitting diode or a radio frequency transmitter.

2. The mote of claim 1, wherein the driver is configured to transmit the recorded data signal from the mote via the first light emitting diode.

3. The mote of claim 1, wherein the driver is configured to transmit the recorded data signal from the mote via the radio frequency transmitter.

4. The mote of claim 1, wherein the optical receiver comprises a photovoltaic diode configured to convert the near infrared light energy to the electrical signal having the supply voltage.

5. The mote of claim 1, wherein the devices include devices of the clock generation circuit and the data recovery circuit.

6. The mote of claim 1, further comprising:
   the electrode, wherein the electrode is a carbon fiber; and
   the first light emitting diode.

7. The mote of claim 1, wherein the optical receiver is configured to wirelessly receive the first power and data signal from a repeater and transmit the recorded data signal to the repeater.

8. The mote of claim 1, wherein the first amplifier is a 3-stage bandpass differential amplifier.

9. The mote of claim 8, wherein the first amplifier comprises a low-nose amplifier, a first voltage gain amplifier and a second voltage gain amplifier.

10. The mote of claim 1, further comprising:
    a non-overlap module configured to, based on a third one of the plurality of clock signals, generate phase signals;
    a current generator configured to, based on the phase signals, generate a current reference;
    a voltage generator configured to, based on the phase signals, generate a voltage reference; and
    the first amplifier is configured to amplify the neuron signal based on the current reference and the voltage reference.

11. The mote of claim 1, further comprising:
    an integration circuit comprising
      a rectifier configured to generate a rectified signal based on the amplified neuron signal, and
      an integrator configured to generate an integrated signal based on the rectified signal; and
    a comparator configured to compare the integrated signal to a voltage threshold and generate a pulsed signal,
    wherein the chip identifier module is configured to generate the recorded data signal based on the pulsed signal.

12. The mote of claim 1, wherein the chip identifier module is configured to encode the recorded data signal based on the chip identifier.

13. The mote of claim 1, wherein the chip identifier module is configured to generate the recorded data signal using symbol interval modulation.

14. The mote of claim 1, further comprising a housing, wherein:
- a volume of the housing is smaller than 250 µm³; and
- the control module, clock generation circuit, data recovery circuit, first amplifier and chip identifier module are disposed in the housing.

15. The mote of claim 14, wherein the housing is 240 µm wide with a height of 220 µm.

16. The mote of claim 1, wherein
- the optical receiver is implemented as a photovoltaic cell and the control module is implemented as a chip; and
- outer top surface dimensions of the photovoltaic cell and the chip are 170 µm×190 µm.

17. The mote of claim 1, wherein the control module comprises the clock generation circuit, data recovery circuit, first amplifier and chip identifier module.

18. A neural recording system comprising:
- the mote of claim 1; and
- a repeater configured to be implanted in the patient, transmit the first power and data signal in form of near infrared light energy to the mote, and receive the recorded data signal in form of near infrared light energy from the mote.

19. The neural recording system of claim 18, wherein the repeater comprises:
- a second light emitting diode configured to emit the first power and data signal; and
- a photodiode configured to detect near infrared light energy associated with the recorded data signal.

20. The neural recording system of claim 19, wherein the photodiode is implemented as a single-photon avalanche diode.

21. The neural recording system of claim 18, wherein:
- the chip identifier module is configured to encode the recorded data signal based on the chip identifier; and
- the repeater is configured to decode the recorded data signal.

22. The neural recording system of claim 18, further comprising an external device configured to be disposed external to the patient and transmit a first radio frequency signal to the repeater, wherein:
- the repeater is configured to convert the first radio frequency signal to the first power and data signal, convert the recorded data signal to a second radio frequency signal, and transmit the second radio frequency signal to the external device.

23. The neural recording system of claim 22, wherein at least one of:
- the repeater is configured to calculate spiking band power corresponding to the neuron signal based on the recorded data signal; or
- the external device is configured to calculate the spiking band power corresponding to the neuron signal based on the second radio frequency signal.

24. The neural recording system of claim 22, wherein at least one of:
- the repeater is configured to make motor predictions based on the recorded data signal; or
- the external device is configured to make motor predictions based on the second radio frequency signal.

25. A neural recording system comprising:
- a plurality of motes including the mote of claim 1, wherein the mote of claim 1 is a first mote, and wherein the plurality of motes comprise a second mote; and
- a repeater configured to
  - be implanted in the patient,
  - transmit the first power and data signal in form of near infrared light energy to the first mote,
  - receive the recorded data signal in form of near infrared light energy from the first mote,
  - transmit a second power and data signal in form of near infrared light energy to the second mote, and
  - receive a second recorded data signal in form of near infrared light energy from the second mote, wherein the second recorded data signal includes a chip identifier of the second mote.

26. The neural recording system of claim 25, further comprising an external device configured to be disposed external to the patient and transmit a first radio frequency signal to the repeater, wherein:
- the repeater is configured to
  - convert the first radio frequency signal to the first power and data signal,
  - covert the first radio frequency signal to the second power and data signal,
  - convert the recorded data signal of the first mote and the second recorded data signal of the second mote to at least one of a second radio frequency signal or a third radio frequency signal, and
  - transmit the at least one of the second radio frequency signal or the third radio frequency signal to the external device; and
- the external device is configured to distinguish data in the at least one of the second radio frequency signal or the third radio frequency signal as being associated with the first mote or the second mote based on at least one of the chip identifier of the first mote, the chip identifier of the second mote or an indication provided by the repeater indicating which portion of the data corresponds to the first mote and which portion of the data corresponds to the second mote.

27. A mote insertion method comprising:
- disposing a plurality of motes in a dissolvable substance, on a multi-layer material stack, or in a mold, wherein the plurality of motes include the mote of claim 1;
- placing the plurality of motes at least partially along an insertion plane defined by the tissue of the patient;
- inserting the electrode of the mote of claim 1 and other electrodes of other ones of the plurality of motes in the tissue; and
- either (i) dissolving the dissolvable substance or (ii) removing the multi-layer material stack or the mold from the plurality of motes.

28. The mote insertion method of claim 27, comprising applying a solvent to dissolve the dissolvable substance.

29. The mote insertion method of claim 28, wherein the dissolvable substance includes polyethylene glycol.

30. The mote insertion method of claim 27, comprising peeling the multi-layer material stack or the mold from the plurality of motes.

31. A mote insertion method comprising:
- disposing a plurality of motes in a dissolvable substance, on a multi-layer material stack, or in a mold, wherein the plurality of motes include the mote of claim 1; and
- placing the plurality of motes at least partially along an insertion plane defined by the tissue of the patient, wherein placing the plurality of motes includes creating a vacuum on a side of one of the plurality of motes to allow lifting and moving of the one of the plurality of motes.

* * * * *

UNITED STATES PATENT AND TRADEMARK OFFICE
CERTIFICATE OF CORRECTION

PATENT NO. : 11,911,128 B2
APPLICATION NO. : 17/173976
DATED : February 27, 2024
INVENTOR(S) : David Blaauw et al.

Page 1 of 1

It is certified that error appears in the above-identified patent and that said Letters Patent is hereby corrected as shown below:

In the Claims

At Column 24, Claim number 11, Line number 51, delete "comprising" and insert --comprising:--.

At Column 25, Claim number 16, Line number 9, delete "wherein" and insert --wherein:--.

At Column 26, Claim number 25, Line number 1, delete "to" and insert --to:--.

At Column 26, Claim number 26, Line number 17, delete "to" and insert --to:--.

At Column 26, Claim number 26, Line number 20, delete "covert" and insert --convert--.

Signed and Sealed this
Sixteenth Day of July, 2024

Katherine Kelly Vidal
*Director of the United States Patent and Trademark Office*